United States Patent
Shoyele

(10) Patent No.: US 11,484,505 B2
(45) Date of Patent: Nov. 1, 2022

(54) DELIVERY COMPOSITIONS, AND METHODS OF MAKING AND USING SAME

(71) Applicant: THOMAS JEFFERSON UNIVERSITY, Philadelphia, PA (US)

(72) Inventor: Sunday Shoyele, Cherry Hill, NJ (US)

(73) Assignee: Thomas Jefferson University, Philadelphia, PA (US)

(*) Notice: Subject to any disclaimer, the term of this patent is extended or adjusted under 35 U.S.C. 154(b) by 549 days.

(21) Appl. No.: 16/340,864

(22) PCT Filed: Oct. 13, 2017

(86) PCT No.: PCT/US2017/056662
§ 371 (c)(1),
(2) Date: Apr. 10, 2019

(87) PCT Pub. No.: WO2018/071864
PCT Pub. Date: Apr. 19, 2018

(65) Prior Publication Data
US 2019/0240164 A1    Aug. 8, 2019

Related U.S. Application Data

(60) Provisional application No. 62/407,604, filed on Oct. 13, 2016.

(51) Int. Cl.
| | |
|---|---|
| *A61K 9/51* | (2006.01) |
| *A61K 31/713* | (2006.01) |
| *A61K 38/16* | (2006.01) |
| *A61K 31/7088* | (2006.01) |
| *A61K 47/64* | (2017.01) |
| *A61K 47/69* | (2017.01) |
| *A61P 11/06* | (2006.01) |
| *A61P 31/14* | (2006.01) |
| *A61P 35/00* | (2006.01) |
| *A61K 38/00* | (2006.01) |
| *B82Y 5/00* | (2011.01) |

(52) U.S. Cl.
CPC ........ *A61K 9/5146* (2013.01); *A61K 31/7088* (2013.01); *A61K 31/713* (2013.01); *A61K 38/16* (2013.01); *A61K 47/64* (2017.08); *A61K 47/6935* (2017.08); *A61P 11/06* (2018.01); *A61P 31/14* (2018.01); *A61P 35/00* (2018.01); *A61K 38/00* (2013.01); *B82Y 5/00* (2013.01)

(58) Field of Classification Search
None
See application file for complete search history.

(56) References Cited

U.S. PATENT DOCUMENTS

| 5,133,908 A | 7/1992 | Stainmesse et al. |
|---|---|---|
| 2005/0056810 A1 | 3/2005 | Bian et al. |
| 2009/0074828 A1* | 3/2009 | Alexis ............ A61P 9/10 514/1.1 |
| 2009/0191277 A1 | 7/2009 | Aimi et al. |
| 2010/0143424 A1 | 6/2010 | Kanazawa et al. |
| 2011/0091565 A1 | 4/2011 | Perumal et al. |
| 2012/0088255 A1 | 4/2012 | Doherty et al. |
| 2012/0195947 A1 | 8/2012 | Perumal et al. |
| 2013/0183368 A1 | 7/2013 | Hutchison et al. |
| 2016/0213777 A1* | 7/2016 | Shoyele ............ A61K 9/145 |

FOREIGN PATENT DOCUMENTS

| WO | 2009135855 A2 | 11/2009 |
|---|---|---|
| WO | 2015038925 A2 | 3/2015 |

OTHER PUBLICATIONS

International Search Report and Written Opinion dated Jan. 18, 2018 for International Appln. No. PCT/US17/56662.
Bailey, et al., "Nanoparticle formulations in pulmonary drug delivery", Med Res Rev. 29(1), 2009, 196-212.
Bromley, et al., "Mechanisms of structure formation in particulate gels of beta-lactoglobulin formed near the isoelectric point", Eur Phys J E Soft Matter. 21(2), 2006, 145-152.
Dim, et al., "Novel Targeted siRNA-Loaded Hybrid Nanoparticles: Preparation, Characterization and in vitro Evaluation", J. Nanobiotechnol., 13:61, 2015.
Jacobsen, et al., "Analysis of miRNA-target interactions across diverse cancer types", Nat. Struct. Mol. Biol., 20, 2013, 1325-1332.
Jain, et al., "Studies on stabilization mechanism and stealth effect of poloxamer 188 onto PLGA nanoparticles", Colloids Surf B Biointerfaces. 109, 2013, 59-67.
Kharbanda, et al., "Muc 1 confers EMT and KRAS independence in mutant KRAS lung cancer cells", Oncotarget, 5, 2014, 8893-8904.
Lakshmikuttyamma, et al., "Stable and efficient transfection of siRNA for mutated KRAS silencing using novel hybrid nanoparticles", Mol Pharm. 11(12), 2014, 4415-4424.
Li, et al., "Controlled release of bevacizumab through nanospheres for extended treatment of age-related macular degeneration", Open Ophthalmol J., 2012, 54-58.
Perepelyuk, et al., "Aptamer-hybrid Nanoparticle Bioconjugate Efficiently Delivers miRNA-29b to Non-Small cell Lung Cancer Cells and Inhibits Growth by Downregulating Essential Oncoproteins", Int. J. Nanomedicine., 11, 2016, 3533-3544.

(Continued)

*Primary Examiner* — Nelson B Moseley, II
(74) *Attorney, Agent, or Firm* — Saul Ewing Arnstein & Lehr LLP; Kathryn Doyle; Domingos J. Silva

(57) ABSTRACT

This invention provides compositions comprising at least one protein nanoparticle comprising a protein and a stealth polymer. In certain embodiments, the nanoparticle further comprises a therapeutic agent, such as but not limited to a miRNA and/or siRNA. In other embodiments, the nanoparticle further comprises a cell surface receptor ligand. Also included in the invention are methods of preparing the compositions of the present invention, and methods of treating, ameliorating or preventing a disease or disorder in a subject using the compositions of the present invention.

14 Claims, 12 Drawing Sheets
Specification includes a Sequence Listing.

(56) References Cited

OTHER PUBLICATIONS

Perepelyuk, et al., "Biodistribution and Pharmacokinetic study of siRNA-loaded anti-NTSR1-mAb-functionalized novel hybrid nanoparticles in metastatic orthotopic murine lung cancer model", Mol. Ther. Nucleic Acids, 5:e282, 2016.

Srinivasan, et al., "Investigation of the stability and cellular uptake of self-associated monoclonal antibody (MAb) nanoparticles by non-small lung cancer cells", Mol Pharm. 10(9), 2013, 3275-3284.

Srinivasan, et al., "Self-associated submicron IgG 1 particles for pulmonary delivery: effects of non-ionic surfactants on size, shape, stability, and aerosol performance", AAPS PharmSciTech.14(1), 2013, 200-210.

Yan, et al., "Microribonucleic acid 29b inhibits cell proliferation and invasion and enhances cell apoptosis and chemotherapy effects of cisplatin via targeting of DNMT3B and AKT3 in prostate cancer", Onco Target Ther., 8, 2015, 557-565.

Yu, et al., "Novel aptamer-nanoparticle bioconjugates enhances delivery of anticancer drug to MUC1-positive cancer cells in vitro", PloS one 6.9: e24077, 2011.

Zhang, et al., "Stealth tanshinone IIA-684 loaded solid lipid nanoparticles: effects of poloxamer 188 coating on in vitro phagocytosis and in vivo pharmacokinetics in rats", Acta Pharm. Sin., 44 (Abstract only), 2009, 1422-1428.

\* cited by examiner 500 nm

25 μm

25 μm

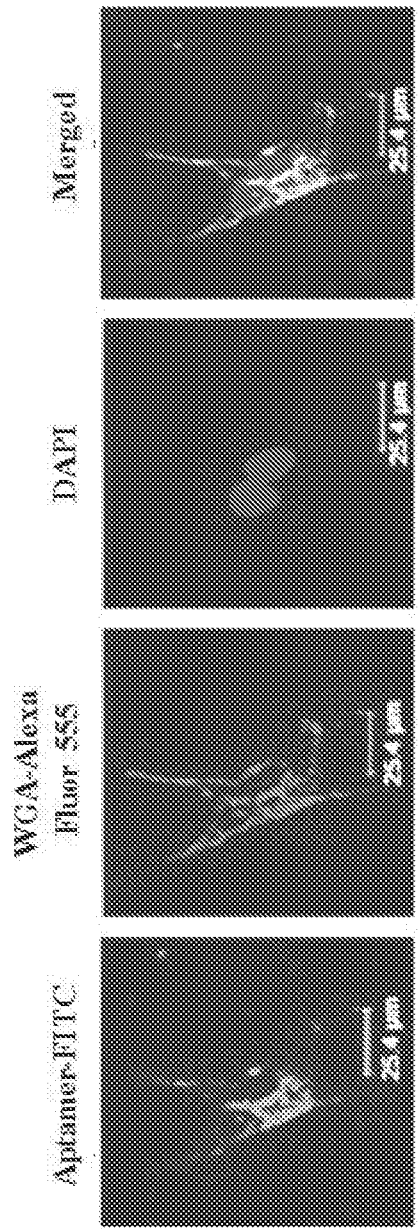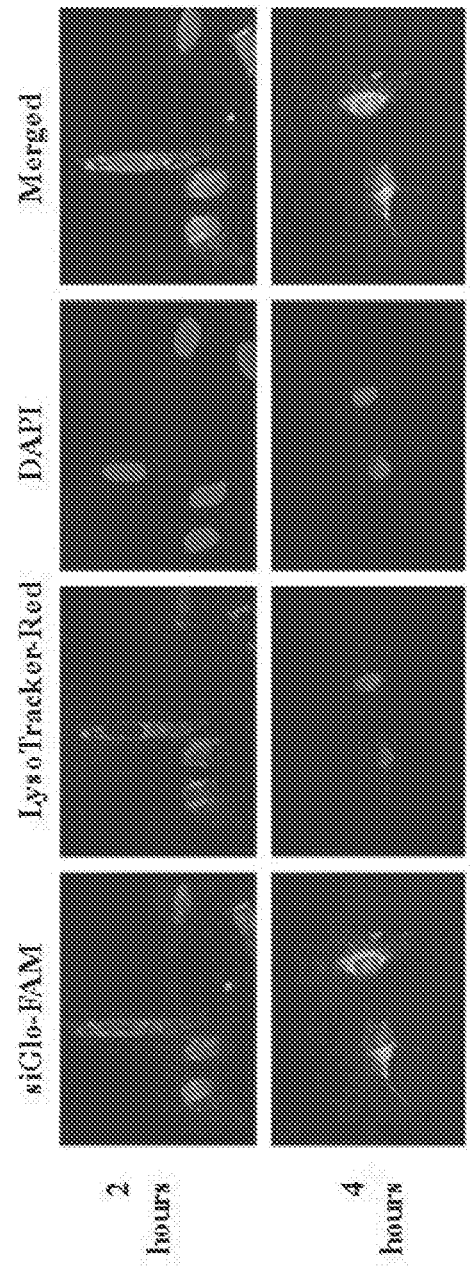

FIG. 8C
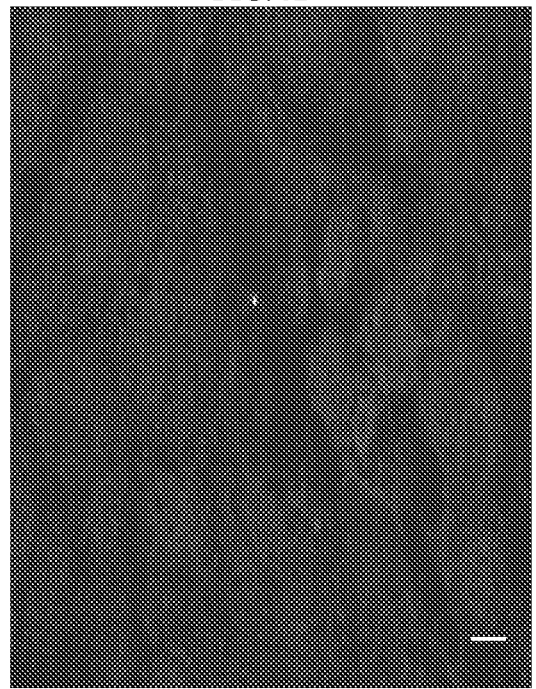
FIG. 8D
FIG. 9
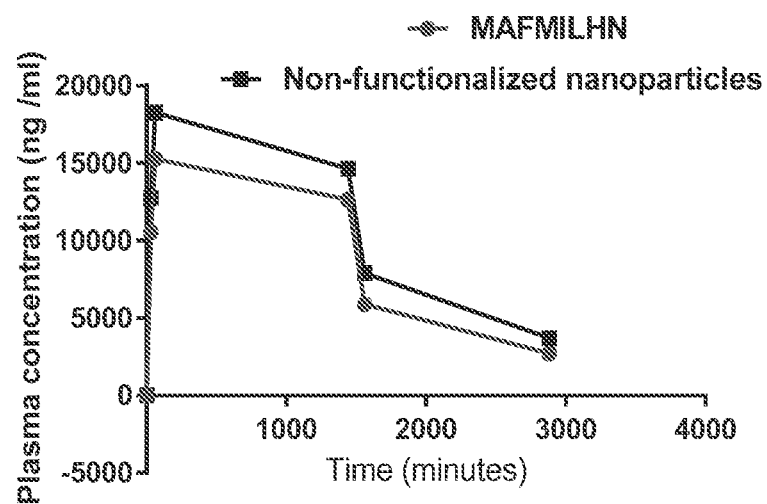

SEQUENCE LISTING

<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: Chemically synthesized

<400> SEQUENCE: 1
gcagttgatc ctttggatac cctgg                                             25

<210> SEQ ID NO 2
<211> LENGTH: 24
<212> TYPE: DNA
<213> ORGANISM: Artificial Sequence
<220> FEATURE:
<223> OTHER INFORMATION: Chemically synthesized

<400> SEQUENCE: 2
tctcaagcag ccagcgcctg cctg                                              24

<210> SEQ ID NO 3
<211> LENGTH: 21
<212> TYPE: DNA
<213> ORGANISM: Artificial Sequence
<220> FEATURE:
<223> OTHER INFORMATION: Chemically synthesized

<400> SEQUENCE: 3
tccccaggtg gcagctgaac c                                                 21

<210> SEQ ID NO 4
<211> LENGTH: 22
<212> TYPE: DNA
<213> ORGANISM: Artificial Sequence
<220> FEATURE:
<223> OTHER INFORMATION: Chemically synthesized

<400> SEQUENCE: 4
ccaaggccaa ccgcgagaag at                                                22

<210> SEQ ID NO 5
<211> LENGTH: 20
<212> TYPE: DNA
<213> ORGANISM: Artificial Sequence
<220> FEATURE:
<223> OTHER INFORMATION: Chemically synthesized

<400> SEQUENCE: 5
ttgctcgaag tccagggcga                                                   20

DELIVERY COMPOSITIONS, AND METHODS OF MAKING AND USING SAME

CROSS-REFERENCE TO RELATED APPLICATIONS

This application is a 35 U.S.C. § 371 national phase application from, and claims priority to, International Application No. PCT/US2017/056662, filed Oct. 13, 2017, and published under PCT Article 21(2) in English, which claims priority to U.S. Provisional Application No. 62/407,604, filed Oct. 13, 2016, all of which are incorporated herein by reference in their entireties.

BACKGROUND OF INVENTION

Proteins are chief players in cellular metabolism, being regularly used as therapeutic agents in medicine. Native or recombinant proteins, along with monoclonal antibodies (mAbs), are examples of therapeutically relevant proteins. However, proteins in general are poorly absorbed across biological membranes, and are thus generally delivered intravenously. Parenteral administration route has several disadvantages, including patient discomfort, potential high cost, and the risk of needle-stick injuries. Pulmonary administration route offers an excellent alternative for proteins (especially antibodies) targeted towards local lung diseases. Monoclonal antibodies such as bevacizumab, anatumomab, benralizumab, enokizumab, mitumomab, oxelumab and palivizumab have gained FDA approval for the treatment of lung diseases, such as asthma, lung cancers and respiratory syncytial virus infection.

Microparticles (rather than nanoparticles) are the particles of choice for delivering drugs (including proteins) to the lung by inhalation, due to the widespread belief that nanoparticles are in a size range not suitable for deep lung delivery. On the other hand, nanoparticles in pulmonary drug delivery may offer advantages such as: (1) potential to achieve relatively uniform distribution of drug dose among the alveoli; (2) enhanced solubility of the drug as compared to its aqueous solubility; (3) decreased incidence of side effects; (4) improved patience compliance; and (5) potential of drug internalization by cells.

Monoclonal antibodies (mAbs) currently do not benefit fully from the unique advantages offered by nanosystems in pulmonary drug delivery, mainly because of the labile nature of their higher order structures, which are not compatible with stresses involved in nanoparticle fabrication.

Bevacizumab, a humanized mAb against vascular endothelial growth factor (VEGF), has shown encouraging signs in the treatment of non-small cell lung cancer (NSCLC) when used alone or in combination with chemotherapy. It was approved in 2006 for use along with paclitaxel and carboplatin as first-line treatment for those with advanced NSCLC. Cancer cells tend to overexpress VEGF, a potent stimulator of angiogenesis, facilitating cancer growth and metastasis. Internalization of bevacizumab into cancer cells is highly important, as intracellular pool of VEGF could be responsible for resistance to bevacizumab in cancer therapy. To this end, intracellular VEGF provides a compelling target for mAbs in cancer therapy.

RNA interference (RNAi) is a very effective tool in the knockdown of specific oncogenes in cancer cells. siRNA is the most widely studied form of RNAi, and has a promising therapeutic potential in cancer and other diseases such as autoimmune diseases and infectious diseases. Nevertheless, challenges still occur in the development of siRNA as a therapeutic agent due to siRNA's susceptibility to enzymatic degradation in blood, non-specific uptake by cells, and the difficulty involved in its transfection into cells due to its relatively large size and polarity. Clearance by the reticuloendothelial system (RES) is another limiting factor affecting the possible therapeutic application of siRNA.

To achieve an efficient knockdown by siRNA, various types of delivery systems have been investigated. Use of viral vectors are hampered by the possibility of viral toxicity and immunogenic and inflammatory reactions. Non-viral vectors such as lipid-based nanoparticles and mesoporous silica are being investigated as possible delivery systems for efficient siRNA transfection. In order to achieve an efficient delivery of siRNA, the delivery system must have the following properties: protect siRNA from nuclease degradation during transportation in systemic circulation; have minimal RES uptake, thereby allowing for long blood circulation time; allow for effective endosomal escape following internalization by host cells; and most important, must not elicit immunological and inflammatory reaction. Lipid nanoparticles demonstrate major limitations: siRNA delivery by lipid-based nanoparticles is substantially reduced, because approximately 70% of the internalized siRNA undergoes exocytosis through egress of the lipid nanoparticles from late endosomes and lysosomes. Use of poly (D,L)-lactide-co-glycolide (PLGA) nanoparticles to deliver siRNA is also problematic, because this polymer is negatively charged and interacts minimally with negatively charged siRNA, thus reducing cellular internalization. There is thus a growing need for a smart nanoparticle delivery system for efficient and stable siRNA transfection.

MicroRNAs (miRNAs) are frequently utilized as research tools within the broad borders of gene therapy and the emerging field of molecular medicine. Although most of the miRNAs are in early stages of clinical trials, these classes of compounds have emerged in recent years as extremely promising candidates for drug therapy to a wide range of diseases, including cancer, infectious diseases, diabetes, cardiovascular, inflammatory, and neurodegenerative diseases, cystic fibrosis, hemophilia, and other genetic disorders. Due to their short sequence, miRNA are often able to form a perfect base-pairing with target messenger RNA (mRNA) to mediate mRNA degradation. Often, one miRNA is able to bind to a number of mRNA transcripts enabling the blockade of numerous pathways that modulate cell proliferation, differentiation, apoptosis and invasion.

miRNA-29b is an epi-miRNA that targets DNA methyltranferases (DNMTs) and regulates DNA demethylation, thus leading to down-regulation of global DNA methylation in malignant cells. Specifically, down-regulation of DNMT3B led to inhibition of cell proliferation and apoptosis of non-small cell lung cancer (NSCLC) cells. In view of this, miRNA-29b is seen as an attractive candidate for miRNA-based therapeutics in NSCLC due to its potent tumor suppressant capabilities. They have the ability to silence critical molecular pathways and possibly enhance the sensitivity of NSCLC to conventional chemotherapeutic agents. However, translational application of this relatively novel therapeutic is limited by many challenges, including degradation in serum, rapid blood clearance, stimulation of immune response, off-target effects, and poor cellular uptake. In order to fully harness this treatment modality in NSCLC, a smart nanoparticle delivery system must be developed in tandem with the development of miRNAs.

Presently, nanoparticulate systems used in drug delivery include: polymer-based drug carriers (including polymeric nanospheres, polymeric micelles and dendrimers), liposomes, viral nanoparticles, and carbon tubes. The processes involved in the fabrication of these nanoparticles often lead to degradation and sometimes loss of biological activity in the biological agent. Further, some materials used to formulate these nanoparticles may have toxic effects and may not be viable in therapeutic treatments.

There is thus a need in the art for novel and versatile delivery compositions that are compatible with biological systems and therapeutic agents. There is a further need for novel compositions and formulations that allow for pulmonary delivery of therapeutically useful proteins, such as native or recombinant proteins or monoclonal antibodies. There is a further need for novel compositions and formulations that allow for efficient and stable miRNA or siRNA transfection. The present invention satisfies these needs.

BRIEF SUMMARY OF THE INVENTION

The invention provides a protein-containing nanoparticle, as well as a composition comprising the same, as well as a method of making the same. The invention further provides a method of treating, ameliorating or preventing a disease or disorder in a subject in need thereof, comprising administering to the subject a pharmaceutically effective amount of a nanoparticle and/or a composition of the invention. The invention further provides a kit comprising a composition comprising a nanoparticle and/or a composition of the invention. The invention further provides a kit comprising a stealth polymer, a protein conjugated with a cell surface receptor ligand, an applicator, and an instructional material for the use of the kit.

In certain embodiments, the core of the nanoparticle comprises at least one protein selected from the group consisting of a plasma protein, an IgG, a cytokine, an immunomodulator, an antigen, a hormone, and an enzyme. In other embodiments, the at least one protein is in a neutral state in the nanoparticle. In yet other embodiments, the nanoparticle is surrounded by a layer comprising a stealth polymer. In yet other embodiments, the at least one protein is conjugated with at least one cell surface receptor ligand, wherein at least a fraction of the ligand is displayed on the outer surface of the surrounding layer of the nanoparticle.

In certain embodiments, the stealth polymer is at least one selected from the group consisting of an alkyl polyethylene glycol, an alkylphenol oxide, a copolymer of polyethylene glycol and polypropylene oxide, a polyethylene glycol, a polypropylene glycol, a polyvinylpyrrolidone (PVP), a polyvinyl alcohol, or any combinations thereof.

In certain embodiments, the nanoparticle has a diameter ranging from about 10 nm to about 1,000 nm. In other embodiments, the nanoparticle has a diameter ranging from about 100 nm to about 500 nm.

In certain embodiments, the plasma protein is at least one selected from the group consisting of albumin, fibrinogen, and globulin. In other embodiments, the cytokine comprises at least one selected from the group consisting of interleukin, erythropoietin, interferon, and filgrastim. In yet other embodiments, the protein comprises IgG. In yet other embodiments, the gG is human.

In certain embodiments, the protein nanoparticle is prepared by a method comprising: adjusting the pH of a first solution comprising a protein to about the isoelectric point of the protein, thereby forming a first protein nanoparticle, which comprises at least a fraction of the protein; wherein, if the protein in the first protein nanoparticle is not conjugated to at least one cell surface receptor ligand, the protein in the first protein nanoparticle is further conjugated with the at least one cell surface receptor; and contacting the first protein nanoparticle with a second solution comprising a stealth polymer, wherein the concentration of the stealth polymer in the second solution ranges from about 0.1% to about 20,000% of the CMC of the stealth polymer, thereby forming at least one protein nanoparticle.

In certain embodiments, the first solution further comprises at least one therapeutic agent, and wherein the first protein nanoparticle comprises at least a fraction of the at least one therapeutic agent. In other embodiments, the at least therapeutic agent is selected from the group consisting of an organic compound, inorganic compound, pharmacological drug, antibody, radiopharmaceutical, protein, peptide, polysaccharide, nucleic acid, siRNA, miRNA, RNAi, short hairpin RNA, antisense nucleic acid, ribozyme and dominant negative mutant. In yet other embodiments, the at least one therapeutic agent comprises a miRNA or siRNA. In yet other embodiments, the antibody comprises a monoclonal antibody. In yet other embodiments, the monoclonal antibody comprises at least one selected from the group consisting of bevacizumab, anatumomab, benralizumab, enokizumab, mitumomab, oxelumab, and palivizumab.

In certain embodiments, at least a fraction of the at least one cell surface receptor ligand is displayed on the outer surface of the stealth polymer coating of the nanoparticle. In other embodiments, the at least one cell surface receptor ligand binds to at least one selected from the group consisting of neurotensin receptor-1, human epidermal growth factor receptor-2 (HER-2), folate receptor, insulin-like growth receptor (IGF), and epidermal growth factor receptor (EGFR).

In certain embodiments, the stealth polymer comprises at least one selected from the group consisting of an alkyl polyethylene glycol, an alkylphenol oxide, a copolymer of polyethylene glycol and polypropylene oxide, a polyethylene glycol, a polypropylene glycol, a polyvinylpyrrolidone (PVP), a polyvinyl alcohol, or any combinations thereof. In other embodiments, the alkyl polyethylene oxide comprises at least one selected from the group consisting of a diethylene glycol hexadecyl ether, polyethylene glycol oleyl ether, diethylene glycol octadecyl ether, polyoxyethylene stearyl ether, polyethylene glycol hexadecyl (cetyl) ether, polyethylene glycol dodecyl (lauryl) ether, decaethylene glycol oleyl ether, polyethylene glycol octadecyl ether, and polyethylene glycol octadecyl ether.

In certain embodiments, the average diameter of the at least one protein nanoparticle ranges from about 10 nm to about 1,000 nm. In other embodiments, the average diameter of the at least one protein nanoparticle ranges from about 100 nm to about 900 nm. In yet other embodiments, the concentration of the stealth polymer in the second solution ranges from about 100% to about 20,000% of the CMC of the stealth polymer. In yet other embodiments, the concentration of the stealth polymer in the second solution ranges from about 300% to about 10,000% of the CMC of the stealth polymer. In yet other embodiments, the concentration of the stealth polymer in the second solution ranges from about 300% to about 5,000% of the CMC of the stealth polymer. In yet other embodiments, the composition further comprises a pharmaceutically acceptable carrier.

In certain embodiments, the method of preparing at least one stealth polymer-coated protein nanoparticle comprises adjusting the pH of a first solution comprising a protein to about the isoelectric point of the protein, thereby forming a first protein nanoparticle, which comprises at least a fraction of the protein. In other embodiments, if the protein in the first protein nanoparticle is not conjugated to at least one cell surface receptor ligand, the protein in the first protein nanoparticle is further conjugated with the at least one cell surface receptor. In yet other embodiments, the method of preparing at least one stealth polymer-coated protein nanoparticle comprises contacting the first protein nanoparticle with a second solution comprising a stealth polymer, wherein the concentration of the stealth polymer in the second solution ranges from about 0.1% to about 20,000% of the CMC of the stealth polymer.

In certain embodiments, the at least one stealth polymer-coated protein nanoparticle is further purified to remove protein or stealth polymer that is not associated with the at least one stealth polymer-coated protein nanoparticle, thereby generating a composition comprising the at least one stealth polymer-coated protein nanoparticle. In other embodiments, the composition comprising at least stealth polymer-coated nanoparticle is further lyophilized.

In certain embodiments, the method of treating, ameliorating or preventing a disease or disorder in a subject in need thereof comprises administering to the subject a pharmaceutically effective amount of a nanoparticle or composition of the invention, further wherein the composition is administered to the subject by an intrapulmonary, intrabronchial, inhalational, intranasal, intratracheal, intravenous, intramuscular, subcutaneous, topical, transdermal, oral, buccal, rectal, pleural, peritoneal, vaginal, epidural, otic, intraocular, or intrathecal route. In other embodiments, the composition is administered to the subject by an intrapulmonary, intrabronchial, inhalational, intranasal, intratracheal, intravenous, intramuscular, subcutaneous or topical route. In yet other embodiments, the composition further comprises at least one therapeutic agent, which is within the protein nanoparticle. In yet other embodiments, the at least therapeutic agent is selected from the group consisting of an organic compound, inorganic compound, pharmacological drug, antibody, radiopharmaceutical, protein, peptide, polysaccharide, nucleic acid, siRNA, RNAi, short hairpin RNA, antisense nucleic acid, ribozyme and dominant negative mutant. In yet other embodiments, the at least therapeutic agent comprises a siRNA or miRNA.

In certain embodiments, the protein comprises IgG. In other embodiments, the nanoparticle further comprises a therapeutic agent comprising a siRNA or a miRNA. In yet other embodiments, the stealth polymer comprises a copolymer of polyethylene oxide and polypropylene oxide. In yet other embodiments, the at least one cell surface receptor ligand binds to at least one selected from the group consisting of neurotensin receptor-1, human epidermal growth factor receptor-2 (HER-2), folate receptor, insulin-like growth receptor (IGF), and epidermal growth factor receptor (EGFR). In yet other embodiments, the disease or disorder is selected from the group consisting of colon cancer, rectum cancer, lung cancer, glioblastoma, renal cell cancer, non-small cell lung cancer, small cell lung cancer, asthma, respiratory syncytial virus (RSV) infection, and any combinations thereof. In yet other embodiments, the disease or disorder comprises a cancer comprising a KRAS mutation. In yet other embodiments, the subject is a mammal. In yet other embodiments, the mammal is human.

In certain embodiments, the kit further comprises an applicator; and an instructional material for the use of the kit, wherein the instruction material comprises instructions for treating, ameliorating or preventing a disease or disorder in a subject in need thereof. In other embodiments, the stealth polymer-containing protein nanoparticle further comprises at least one therapeutic agent.

In certain embodiments, the instruction material comprises instructions for preparing a stealth polymer-coated protein nanoparticle wherein at least a fraction of the ligand is displayed on the outer surface of the stealth polymer coating of the nanoparticle.

BRIEF DESCRIPTION OF THE DRAWINGS

For the purpose of illustrating the invention, there are depicted in the drawings certain embodiments of the present invention. However, the invention is not limited to the precise arrangements and instrumentalities of the embodiments depicted in the drawings.

FIG. 1A comprises a non-limiting schematic of an aptamer-functionalized hybrid nanoparticle. FIG. 1B comprises a scanning electron micrograph of miRNA-loaded hybrid nanoparticles (scale bar: 500 nm). FIG. 1C comprises a fluorescence micrograph of FITC-MUC1 aptamer-functionalized hybrid nanoparticles (scale bar: 25 μm). FIG. 1D comprises a fluorescent micrograph of non-functionalized hybrid nanoparticles (scale bar: 25 pin). FIG. 1E comprises FT-IR spectra of various nanoparticles to confirm the conjugation of aptamer to the nanoparticles.

FIG. 3A illustrates reverse transcriptase PCR showing levels of expression of MUC1 in selected cells (n=3). FIG. 3B illustrates comparison of nanoparticle internalization by A549 and MRC-5 using flow cytometry. **P≤0.001, n=3. FIG. 3C is a graph illustrating mean fluorescence intensity for non-inhibited nanoparticles and MUC1-inhibited nanoparticles.

FIGS. 4A-4B comprise a series of images illustrating fluorescence microscopy of nanoparticle—cell membrane interaction. FIG. 4A comprises a series of micrographs showing the interaction between FITC-MUC1 aptamer-functionalized nanoparticles and cell membrane after 2-hour incubation. FIG. 4B comprises a series of micrographs showing intracellular trafficking of internalized siGLO-FAM-loaded nanoparticles.

FIG. 5A illustrates downregulation of DNMT3B by miRNA-29b nanoparticles. FIG. 5B illustrates downregulation of MCL1 by miRNA-29b nanoparticles. miR-29b-nano represents MUC1 aptamer-functionalized miRNA-29b-loaded hybrid nanoparticles; NC-nano represents MUC1 aptamer-functionalized negative control miRNA-loaded hybrid nanoparticles; miR-29b-lipo represents lipofectamine 200-transfected miRNA-29b. FIG. 5C illustrates cell death detection ELISA showing the induction of apoptosis in A549 cells (n=3). FIG. 5D illustrates antiproliferative effect of miRNA-29b nanoparticles in A549 cells (n=5).

FIG. 7A: MUC1-aptamer functionalized miR-29b-loaded hybrid nanoparticles (MAFMILHN). FIG. 7B: non-functionalized miR-29b-loaded hybrid nanoparticles. FIG. 7C: untreated A549 cells. FIG. 7D: untreated MRC-5 cells. FIG. 7E: MAFMILHN-treated A549 cells. FIG. 7F: non-functionalized miR-29b-loaded hybrid nanoparticle-treated A549 cells. FIG. 7G: MAFMILHN-treated MRC-5 cells. FIG. 7H: non-functionalized miR-29b-loaded hybrid nanoparticle-treated MRC-5 cells. Arrows depict MAFMILHN in cells.

FIGS. 8A-8D illustrate tissue distribution of MAFMILHN in the lung of tumor bearing mice. FIG. 8A: MAFMILHN. FIG. 8B: Non-functionalized miR-29b-loaded hybrid nanoparticles. FIG. 8C: Hyperspectral imaging of MAFMILH. FIG. 8D: Hyperspectral imaging of Non-functionalized miR-29b-loaded hybrid nanoparticles. Scale bar=10 µm.

FIG. 9 is a graph illustrating miRNA-27b plasma concentration over time. Tumor bearing mice were given a single dose of 1.5 mg/kg of miRNA-29b in MAFMILHN or in non-functionalized miRNA-29b-loaded hybrid nanoparticles. n=3.

FIG. 10A: Evaluation of apoptosis using TUNEL. FIG. 10B: Evaluation of apoptosis using cell death detection ELISA, ***p≤0.001, n=3.

FIG. 11A: Graph of tumor burden over four week period. FIG. 11B: Representative bioluminescence images of tumor-bearing mice.

DETAILED DESCRIPTION OF INVENTION

Figure 1A:
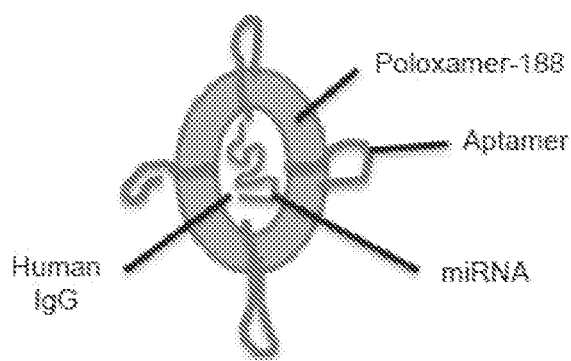
FIGS. 1A-1E comprises a set of images and graphs illustrating hybrid nanoparticle characterization.

The present invention relates in part to the unexpected discovery of novel protein nanoparticles, as well as methods of making the same. In one aspect, the methods of the present invention allow for careful control of the content, size and shape of the nanoparticles, thus enhancing their overall drug delivery properties.

In certain embodiments, the methods of the present invention provide nanoparticles with distinct compositions, improved loading capacity, and/or lower particle size as compared to the methods disclosed in US20160213777, which is incorporated herein in its entirety by reference.

In certain embodiments, particle sizes of the nanoparticles obtained using the methods of the present invention are smaller than those obtained with the methods of the prior art. In other embodiments, particle sizes of the nanoparticles obtained using the methods of the present invention are equal to or lower than 1,000 nm, 900 nm, 800 nm, 700 nm, 600 nm, 500 nm, 400 nm, 300 nm, 200 nm, 190 nm, 180 nm, 170 nm, 160 nm, 150 nm, 140 nm, 130 nm, 120 nm, 110 nm, 100 nm, 90 nm, 80 nm, 70 nm, 60 nm, and/or 50 nm.

In certain embodiments, the nanoparticle of the invention comprises a core comprising a protein (such as but not limited to a plasma protein, an IgG, a cytokine, an immunomodulator, an antigen, a hormone, and/or an enzyme), which is in a neutral state (i.e., the overall charge of the protein within the nanoparticle is zero or nearly zero). In other embodiments, the nanoparticle of the invention is surrounded by a stealth polymer layer (or stealth polymer coating), which comprises for example an alkyl polyethylene glycol, an alkylphenol oxide, a copolymer of polyethylene glycol and polypropylene oxide (such as, but not limited to, a poloxamer), a polyethylene glycol, a polypropylene glycol, a polyvinylpyrrolidone (PVP), a polyvinyl alcohol, or any combinations thereof. In yet other embodiments, the nanoparticle of the invention comprises at least one cell surface receptor ligand, wherein at least a fraction of the ligand is displayed on the surface of the nanoparticle. In yet other embodiments, at least a portion of the cell surface receptor ligand spans the stealth polymer layer. In yet other embodiments, the at least one cell surface receptor ligand is conjugated to the protein via non-covalent bond(s). In yet other embodiments, the at least one cell surface receptor ligand is conjugated to the protein via covalent bond(s). In yet other embodiments, the at least one cell surface receptor ligand is conjugated to the protein before the protein is coated with the stealth polymer. In yet other embodiments, the at least one cell surface receptor ligand is conjugated to the protein before the protein nanoparticle is formed. In yet other embodiments, the at least one cell surface receptor ligand is conjugated to the protein after the protein nanoparticle is formed, but before the protein is coated with the stealth polymer.

In certain embodiments, the nanoparticles of the invention comprise a poloxamer, which helps achieve stable and efficient delivery of nucleic acid-based therapeutics. In other embodiments, the core of the nanoparticles comprises a protein, such as but not limited to human IgG, which is a main encapsulating component of these hybrid nanoparticles. Without wishing to be limited by any theory, the protein helps to reduce/eliminate well-documented immunogenic reaction experienced with most nanoparticle formulations, by "deceiving" the body to believe that the nanoparticles are natural components of the blood. In yet other embodiments, the outer layer of these hybrid nanoparticles is composed of poloxamer, a nonionic triblock copolymer, which helps to circumvent the reticuloendothelial system during systemic circulation, acting as a stealth polymer by preventing macrophage uptake during circulation.

In certain embodiments, the nanoparticles of the invention are functionalized on their surface with at least one cell surface receptor ligand, such as, but not limited to a MUC1-aptamer. In other embodiments, the ligand facilitates active targeting of the nanoparticle to the surface receptor-expressing cells, while avoiding undesirable accumulation in cells that do not express such surface receptors.

In certain embodiments, a method of the invention comprises providing a solution comprising a protein of interest, and optionally at least one therapeutic agent, and titrating the solution to about the isoelectric point of the protein, thereby forming a precipitate comprising the protein nanoparticle, wherein the protein nanoparticle comprises at least a fraction of the protein (and at least a fraction of the therapeutic agent, if the at least one therapeutic agent is present in the solution). The protein nanoparticle is optionally purified; in a non-limiting example, the protein nanoparticle is washed with a solvent, such as but not limited to water. The protein nanoparticle is then resuspended in a solution comprising a stealth polymer, wherein the concentration of the stealth polymer in the solution ranges from about 0.1% to about 20,000% of the CMC of the stealth polymer, and optionally at least one therapeutic agent. The resulting stealth polymer-containing protein nanoparticle can then be purified and/or isolated from the solution. Optionally, a cell surface receptor ligand is present in the protein nanoparticle and/or the stealth polymer-coated protein nanoparticle.

In certain embodiments, the nanoparticles of the present invention have improved aerosolization properties as compared to irregularly shaped (>20 µm) unprocessed particles. In other embodiments, the nanoparticles of the present invention comprise at least one therapeutic agent, wherein the at least one therapeutic agent within the nanoparticles has improved pharmacokinetics as compared to the "unformulated" therapeutic agent (i.e., the therapeutic agent that is not within the nanoparticles of the present invention). In yet other embodiments, the nanoparticles of the present invention further comprise a cell surface receptor ligand, which allows for the nanoparticles to recognize and bind to a cell that displays such cell surface receptor.

In certain embodiments, the protein comprises a native or recombinant therapeutically useful protein, such as plasma proteins like albumins, fibrinogen and clotting factors; hormones like insulin, glucagon, and somatropin; immunomodulators like cyclosporine; cytokines like interleukin, erythropoietin, interferon, and filgrastim; enzymes like blood clotting factors, adenosine deaminase, alpha1 antitryptin; and peptide vaccines. In other embodiments, the protein comprises an antibody. In yet other embodiments, the protein comprises an immunoglobulin. In yet other embodiments, the immunoglobulin comprises IgA, IgD, IgE, IgG, and/or IgM. In yet other embodiments, the antibody comprises a monoclonal antibody (mAb).

Potential applications of the mAb nanoparticles of the present invention include, in a non-limiting manner, selective targeting of intracellular oncoproteins in cancer; pulmonary delivery of mAb by dry powder inhalation and pressurized metered dose inhalation and nebulizers; as a carrier system for delivering nucleic acids and/or small molecule to cells; and formulation of high concentration mAb dosage forms for various diseases.

Non-Limiting Disclosure

The therapeutic efficacy and pharmacokinetics of mucin1-aptamer functionalized miRNA-29b-loaded hybrid nanoparticles (MAFMILHN) in lung tumor-bearing SCID mice was evaluated, as described herein. MAFMILHN were manufactured using an iso-electric point based nanotechnology. They were then fully characterized for particle size, Zeta potential, loading capacity and encapsulation efficiency. The ability of MAFMILHN to downregulate oncoprotein DNMT3B both at the cellular level and in vivo was monitored using western blot, while the effect of the downregulation of DNMT3B was assessed using bioluminescence. Results indicate that the presence of MUC1-aptamer on the surface of the nanoparticles enhanced the selective delivery of miRNA-29b to tumor cells and tissues. Further, the downregulation of DNMT3B by MAFMILHN resulted to the inhibition of tumor growth in mouse models. The present studies indicate that the MAFMILHNs selectively deliver miRNA-29b to lung tumor while limiting accumulation in healthy tissues. In certain non-limiting embodiments, very limited expression of MUC1 in healthy tissues enables selective accumulation of miRNA-29b loaded hybrid nanoparticles in NSCLC while avoiding healthy tissues. In other non-limiting embodiments, delivery of MAFMILHNs lead to in vivo downregulation of DNMT3B, leading to regression of NSCLC in orthotopic mouse models.

Translational application of miRNA-based therapeutics is limited by a lack of smart nanoparticle delivery system to selectively deliver these molecules intracellularly to cancer cells. As a demonstrated herein, a hybrid nanoparticles delivery system, which is capable of safe and effective delivery of nucleic acid-based therapeutics, was functionalized with MUC1 aptamer to enable selective delivery of miRNAs to NSCLC cells. miRNA-29b was selected as a model miRNA, because miRNA-29b, a tumor suppressor miRNA, is aberrantly expressed in NSCLC and its perturbation is related to tumor development and progression. miRNA-29b was thus an attractive candidate for miRNA-based therapeutics in NSCLC. The presence of MUC1, a transmembrane protein that is aberrantly overexpressed in NSCLCs, allows for the active targeting of payload to lung adenocarcinomas. MUC1 has been shown to be overexpressed in 80% of lung adenocarcinoma.

Hybrid nanoparticles comprising human IgG and poloxamer-188 were prepared using an isoelectric point (pI)-based nanoprecipitation technology. This technology is based on the fact that proteins (human IgG) have minimum solubility but maximum precipitation at their pI. Nanoparticles produced using this technology are characteristically spherical in morphology (FIG. 1B). The particles were negatively charged possibly because of the presence of residual miRNA on the surface of the nanoparticles. However, the charge on the particles became positive following the conjugation of aptamer to the surface of the nanoparticles. Without wishing to be limited by any theory, the positive charge is attributed at least in part to the presence of an amino group $NH_2$ in the aptamer to facilitate the conjugation reaction. Both fluorescence microscopy and FT-IR analysis were performed to confirm the successful conjugation of MUC1 aptamer to the preformed hybrid nanoparticles. As shown in FIG. 1C, FITC-labeled MUC1 aptamer present on the surface of the hybrid nanoparticles led to the presence of green color in the MUC1 aptamer-functionalized hybrid nanoparticles. In contrast, non-functionalized hybrid nanoparticles did not show any green color in FIG. 1D. FT-IR data in FIG. 1E demonstrate a distinctive difference between the spectra of MUC1 aptamer-functionalized hybrid nanoparticles and the non-functionalized hybrid nanoparticles. Non-functionalized hybrid nanoparticles had a peak at about 3,274 $cm^{-1}$, which can be attributed to the group stretching vibration of both $NH_2$ and OH in the human IgG. Following the conjugation of MUC1 aptamer to the hybrid nanoparticles, this peak became sharper and more intense due to the presence of additional $NH_2$ and OH stretching vibration attributable to the conjugation of $NH_2$ aptamer to the hybrid nanoparticles. Both MUC1 aptamer-functionalized and non-functionalized nanoparticles showed a peak at about 1,541 $cm^{-1}$, which can be attributed to the presence of amide II carbonyl stretch from human IgG in both nanoparticles. Furthermore, without wishing to be limited by any theory, the peak at about 1,660 $cm^{-1}$ in the spectra for MUC1 aptamer-functionalized hybrid nanoparticles, but absent in the corresponding non-functionalized hybrid nanoparticles, is attributed to conjugated amide stretching due to the conjugation of the amino group from the aptamer to the carboxyl groups present in human IgG.

Figure 2:
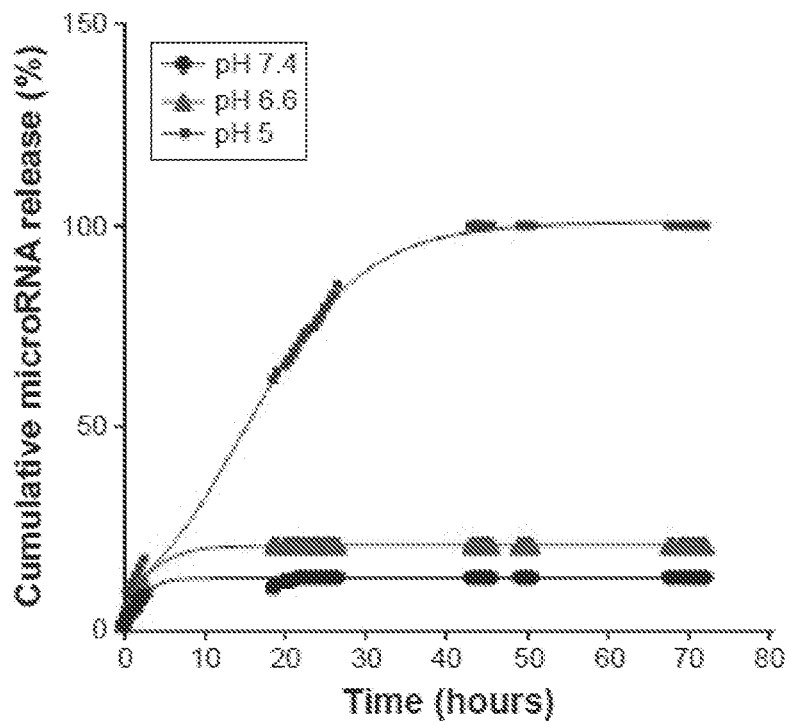
FIG. 2 comprises a graph illustrating in vitro release. Release profiles show that only a limited amount of microRNA-29b was released at pH values 6.6 and 7.4. However, an optimal release was observed at pH 5.

FIG. 2 demonstrates a limitation in the release of miRNA from MUC1 aptamer-functionalized hybrid nanoparticles at pH values 6.6 and 7.4 when compared with the release profile at pH 5. This demonstrates the pH-sensitive nature of these nanoparticle delivery systems. At pH values of 6.6 and 7.4, very limited amount of the loaded miRNA (<20%) was released throughout the study period. The limited release of siRNA at pH values 6.6 and 7.4 could be attributed to the reduced/limited solubility of human IgG at these pH values. Proteins are known to have limited solubility at pH values close to their pI. Since the pI of human IgG is 7, its solubility at neutral pH values is quite limited. This makes it difficult for the encapsulated miRNA to be released at this pH value, hence possibly limiting its release extracellularly in blood and tumor microenvironment. However, at acidic pH value of 5, an optimal miRNA release of about 100% was obtained due to the solubility of human IgG at this pH. An optimum release of the loaded miRNA is very desirable at pH 5, as this pH represents the acidic condition of endosome/lysosome.

Figure 3A:
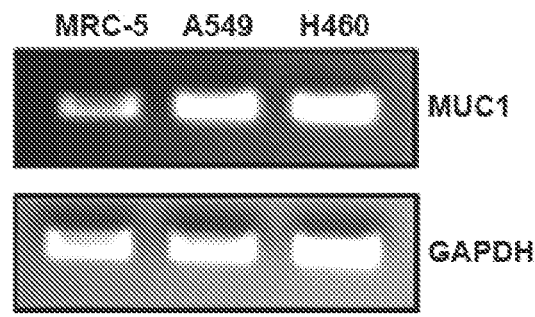
FIGS. 3A-3C comprises a series of images and graphs illustrating impact of MUC1 expression levels on MUC1 aptamer-functionalized hybrid nanoparticle internalization.
Figure 3B:
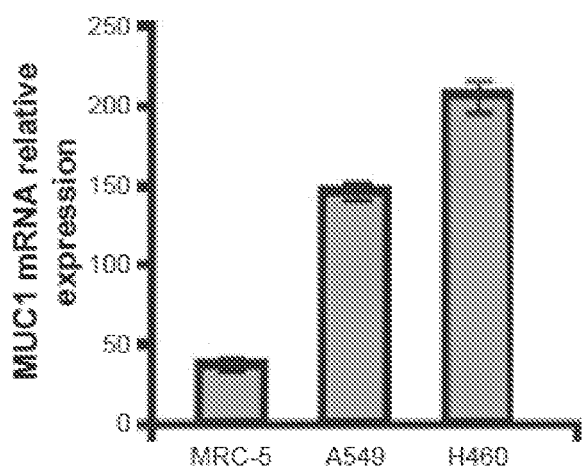
Figure 3C:
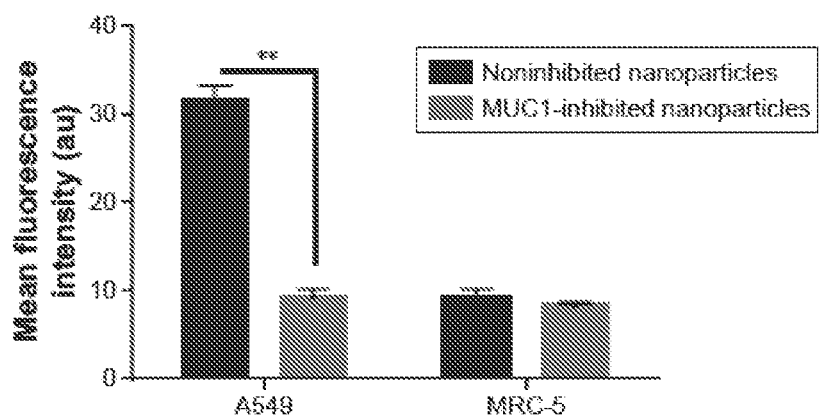

Uptake of MUC1 aptamer-functionalized nanoparticles (FIG. 3B) is significantly higher in A549 cells in comparison to MRC-5 cells. Without wishing to be limited by any theory, the differential internalization of nanoparticles between these cell lines can be attributed at least in part to the differential expression of MUC1 on the surface of these cells. While A549 is an adenocarinoma cell line known to aberrantly overexpress MUC1, MRC-5 is a normal lung fibroblast cell line with limited expression of MUC1 (FIG. 3A). To further confirm the involvement of MUC1 in the internalization of these nanoparticles, cells were pretreated with free MUC1 aptamer prior to their treatment with the MUC1 aptamer-functionalized hybrid nanoparticles to further elucidate the role of MUC1 in uptake of nanoparticles. In FIG. 3B, the significantly lower uptake of nanoparticles by A549 cells following pre-treatment with free MUC1 aptamer can be attributed at least in part to competitive binding of this free MUC1 aptamer to MUC1 on the membrane of the cells, limiting the uptake of MUC1 aptamer-functionalized hybrid nanoparticles. FIG. 4A further demonstrates the interaction between the cell membrane of A549 cells and FITC-MUC1 aptamer conjugated to the hybrid nanoparticles. Presence of green color on the membrane of the A549 cells suggests the binding of these nanoparticles to the membrane prior to internalization.

One of the challenges facing the translational application of nanomedicine is the lack of effective endosomal escape following internalization by host cells. Stable nucleic acid lipid particles, which to date are the most advanced delivery system for nucleic acid, have demonstrated some limitation in recent studies. About 70% of the internalized nucleic acid undergoes exocytosis (endocytic recycling) through egress of the lipid nanoparticles from late endosomes and lysosomes. It is thus important to design nanoparticle delivery system with the ability to escape the recycling pathways. To demonstrate the ability of the hybrid nanoparticles to escape endocytic recycling, intracellular trafficking of internalized nanoparticles was monitored using fluorescence microscopy. In FIG. 4B, colocalization of nanoparticles (green) and endosome (red) indicates the presence of nanoparticles in the late endosome after 2 hours of incubation. However, release of siGLO-FAM (green) can be seen after 4 hours of incubation, indicating the escape of encapsulated siGLO-FAM from late endosomes into the cytosol of the cells. This was possible due to the buffering capacity of the hybrid nanoparticles in the endosome. The solubility of IgG and poloxamer-188 at acidic pH 5, as demonstrated by the in vitro release data in FIG. 2, makes it possible for the dissolved IgG in the endosome to activate the proton pump that raises osmotic pressure in the endosome subsequently leading to the swelling and subsequent escape of siGLO-FAM from the endosomes into the cytoplasm.

Figure 5A:
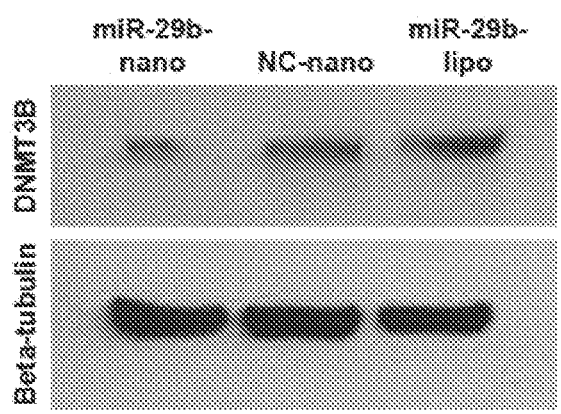
FIGS. 5A-5D comprises a series of images and graphs illustrating effect of miRNA-29b on essential oncoproteins in A549 cells.
Figure 5B:
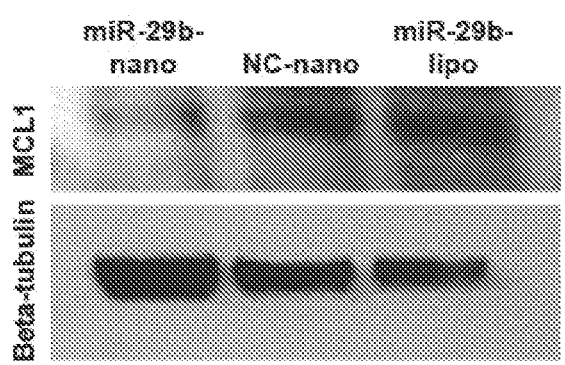

To evaluate the ability of internalized miRNA-29b to downregulate target oncoproteins DNMT3B and MCL1, expression of these proteins was monitored using Western blot. As demonstrated in FIGS. 5A-5B, both target oncoproteins were downregulated in A549 cells following treatment with MUC1 aptamer-functionalized miRNA-29b-loaded hybrid nanoparticles in a superior version when compared with lipofectamine-transfected miRNA-29b. DNMT3B is a member of the DNA methyltransferase family accounting for inactivation of tumor suppressor genes in many cancer cells. miRNA-29b exerts its tumor-suppressive role by directly targeting DNMT3b in cancer cells. Furthermore, miRNA-29b is downregulated in malignant cells, whereas MCL1 is upregulated. MCL1 is a potent antiapoptic protein of the BCL-2 family. Downregulation of both DNMT3B and MCL1 by miRNA-29b inhibits cancer cell growth and promotes apoptosis. However, the challenge facing the clinical application of miRNA-29b to cancer therapy is the availability of an efficient and safe delivery system to enhance intracellular delivery of this potent molecule to cancer cells. FIGS. 5A-5B demonstrates the superior efficiency of MUC1 aptamer-functionalized miRNA-29b-loaded hybrid nanoparticles in downregulating oncoproteins DNMT3b and MCL1 in NSCLC cells over lipofectamine-delivered miRNA-29b. The ability of this treatment modality to induce apoptosis in A549 cells due to downregulation of DNMT3B and MCL1 was also demonstrated in FIG. 5C. MUC1 aptamer miRNA-29b-loaded hybrid nanoparticles also demonstrated superior antiproliferative effect in A549 cells in comparison to NeoFX-delivered miRNA-29b. NeoFX is another commonly used, commercially available nucleic acid transfection agent.

As demonstrated herein, MUC1 aptamer-functionalized hybrid nanoparticle delivery system was successfully prepared. The present results demonstrated that this delivery system can efficiently deliver miRNAs effectively to cancer cells in a superior version compared with commercially available transfection agents. The present results also demonstrated that direct downregulation of DNMT3b and MCL1 led to antiproliferative effect in A549 cells. In certain embodiments, this novel aptamer-hybrid nanoparticle bioconjugate delivery system can serve as a platform for intracellular delivery of miRNAs to cancer cells, hence improving the therapeutic outcome of lung cancer.

Definitions

The definitions used in this application are for illustrative purposes and do not limit the scope used in the practice of the present invention.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, polymer chemistry, and protein chemistry are those well-known and commonly employed in the art.

As used herein, the articles "a" and "an" are used herein to refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody" as used herein refers to an immunoglobulin molecule able to specifically bind to a specific epitope on an antigen. Antibodies can be intact immunoglobulins derived from natural sources or from recombinant sources, and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1998, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antigen" or "Ag" is defined as a molecule that provokes an immune response. This immune response may involve either antibody production, or the activation of specific immunologically-competent cells, or both. The skilled artisan will understand that any macromolecule, such as virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. The present invention includes, but is not limited to, the use of partial nucleotide sequences of more than one gene, and these nucleotide sequences are arranged in various combinations to elicit the desired immune response. Moreover, a skilled artisan will understand that an antigen need not be encoded by a "gene" at all. An antigen can be generated, synthesized or derived from a biological sample. Such biological sample can include, but is not limited to, a tissue sample, tumor sample, cell or biological fluid.

As the term is used herein, "applicator" is used to identify any device including, but not limited to, a hypodermic syringe, pipette, nebulizer, vaporizer and the like, for administering the compounds and compositions used in the practice of the present invention.

As used herein, "aptamer" refers to a small molecule that can bind specifically to another molecule. Aptamers are typically either polynucleotide- or peptide-based molecules. A polynucleotidal aptamer is a DNA or RNA molecule, usually comprising several strands of nucleic acids, that adopts highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

As used herein, the term "BRIJ®" is a trademark that described a non-ionic detergent comprising an oligo- or poly-ethylene glycol mono-derivatized with an aliphatic chain (an alkyl polyethylene oxide). Examples of BRIJ® compounds comprises BRIJ® 52 (polyethylene glycol hexadecyl ether; $M_n$~330), BRIJ® 58 (polyethylene glycol hexadecyl ether; $M_n$~1,124), BRIJ® 93 (polyethylene glycol oleyl ether; $M_n$~357), BRIJ® C10 (polyethylene glycol hexadecyl ether), BRIJ® L4 (tetraethylene glycol dodecyl ether), BRIJ® L23 (tricosethylene glycol dodecyl ether), BRIJ® O10 and BRIJ® O20 (decaethylene glycol oleyl ether), BRIJ® S2 (diethylene glycol octadecyl ether), BRIJ® S10 and BRIJ® S100 (decaethylene glycol octadecyl ether), As used herein, "biologically active" means that the compositions elicit a biological response in a mammal that can be monitored and characterized in comparison with an untreated mammal. In certain embodiments, the compositions are administered to the respiratory tract of the mammal. In other embodiments, the compositions are useful for inhalational, nasal, intrapulmonary, intrabronchial, or inhalation administration. In yet other embodiments, the compositions are useful for nasal, inhalational, topical, oral, buccal, rectal, pleural, peritoneal, vaginal, intramuscular, subcutaneous, transdermal, epidural, intratracheal, otic, intraocular, intrathecal or intravenous administration.

As used herein, the term "CMC" refers to critical micelle concentration. The CMC of a stealth polymer is defined as the solution concentration of the stealth polymer above which stealth polymer micelles form spontaneously. In certain embodiments, additional stealth polymer added to the system beyond the CMC value is incorporated in more micelles.

As used herein, the term "container" includes any receptacle for holding the pharmaceutical composition. For example, in certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well-known in the art. It should be understood that the instructions for use of the pharmaceutical composition may be contained on the packaging containing the pharmaceutical composition, and as such the instructions form an increased functional relationship to the packaged product. However, it should be understood that the instructions can contain information pertaining to the compound's ability to perform its intended function.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount" or "therapeutically effective amount" or "pharmaceutically effective amount" of a composition are used interchangeably to refer to the amount of the composition that is sufficient to provide a beneficial effect to the subject to which the composition is administered.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly five amino acids and/or sugars in size. One skilled in the art understands that generally the overall three-dimensional structure, rather than the specific linear sequence of the molecule, is the main criterion of antigenic specificity and therefore distinguishes one epitope from another.

As used herein, the term "exogenous" refers to any material introduced from or produced outside an organism, cell, tissue or system.

As used herein, the term "heavy chain antibody" or "heavy chain antibodies" comprises immunoglobulin molecules derived from camelid species, either by immunization with an antigen and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

"Instructional material," as that term is used herein, includes a publication, a recording, a diagram, or any other medium of expression which can be used to communicate the usefulness of a composition of the present invention in a kit. The instructional material of the kit may, for example, be affixed to a container that contains a composition of the present invention or be shipped together with a container which contains a composition. Alternatively, the instructional material may be shipped separately from the container with the intention that the recipient uses the instructional material and a composition cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the term "IP-particle" or "IP-nanoparticle" refers to IgG-poloxamer-188 nanoparticle.

As used herein, the term "medical intervention" means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

As used herein, the terms "peptide" and "polypeptide" and "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic has a N-terminus and a C-terminus. The N-terminus has an amino group, which can be free (i.e., as a $NH_2$ group) or appropriately protected (for example, with a BOC or a Fmoc group). The C-terminus has a carboxylic group, which can be free (i.e., as a COOH group) or appropriately protected (for example, as a benzyl or a methyl ester). A cyclic peptide does not necessarily have free N- or C-termini, since they are covalently bonded through an amide bond to form the cyclic structure.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, a "pharmaceutically acceptable carrier" means a pharmaceutically acceptable material, composition or carrier, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. As used herein "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds can also be incorporated into the compositions.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "poloxamer" refers to a non-ionic triblock copolymer composed of a central hydrophobic chain of polyoxypropylene (also known as poly(propylene oxide)) flanked by two hydrophilic chains of polyoxyethylene (also known as poly(ethylene oxide)). Poloxamers are also known by the trade names SYNPERONIC®, PLURONIC®, and KOLLIPHOR®. For the generic term "poloxamer", these copolymers are commonly named with the letter "P" (for poloxamer) followed by three digits, wherein the first two digits×100 represents the approximate molecular mass of the polyoxypropylene core, and the last digit×10 represents the percentage polyoxyethylene content (e.g., P407 is a poloxamer with a polyoxypropylene molecular mass of 4,000 g/mol and a 70% polyoxyethylene content). For the PLURONIC® and SYNPERONIC® trade names, coding of these copolymers starts with a letter to define its physical form at room temperature [L=liquid, P=paste, F=flake (solid)] followed by two or three digits. The first digit in a two-digit number, or the first two digits in a three-digit number, in the numerical designation, multiplied by 300, represents the approximate molecular weight of the hydrophobe; and the last digit×10 represents the percentage polyoxyethylene content (e.g., L61 indicates a polyoxypropylene molecular mass of 1,800 g/mol and a 10% polyoxyethylene content). In certain embodiments, poloxamer 181 (P181), PLURONIC® L61 and SYNPERONIC® PE/L 61 are interchangeable.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease. Disease and disorder are used interchangeably herein.

As used herein, a "prophylactic" or "preventive" treatment is a treatment administered to a subject who does not exhibit signs of a disease or disorder or exhibits only early signs of the disease or disorder for the purpose of decreasing the risk of developing pathology associated with the disease or disorder.

As used herein, the term "RES" refers to reticulo-endothelial system.

By the term "specifically bind" or "specifically binds" as used herein is meant that a first molecule (e.g., an antibody) preferentially binds to a second molecule (e.g., a particular antigenic epitope), but does not necessarily bind only to that second molecule.

As used herein, the term "stealth polymer" refers to a polymer or a surfactant that can be used to coat a particulate object and reduces opsonization of the coated particulate object by phagocytes of the reticulo-endothelial system. In certain embodiments, the stealth polymer coating reduces in vivo engulfment or clearance of the coated particulate object. Non-limiting examples of stealth polymers include an alkyl polyethylene glycol, an alkylphenol oxide, a copolymer of polyethylene glycol and polypropylene oxide (such as, but not limited to, a poloxamer), a polyethylene glycol, a polypropylene glycol, a polyvinylpyrrolidone (PVP), a polyvinyl alcohol, or any combinations thereof.

A "subject" or "individual" or "patient," as used therein, can be a human or non-human mammal. Non-human mammals include, for example, livestock and pets, such as ovine, bovine, porcine, canine, feline and murine mammals. Preferably, the subject is human.

By the term "synthetic antibody" as used herein is meant an antibody generated using recombinant DNA technology, such as, for example, an antibody expressed by a bacteriophage as described herein. The term should also be construed to mean an antibody generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, a "therapeutic" treatment is a treatment administered to a subject who exhibits signs of pathology of a disease or disorder for the purpose of diminishing or eliminating those signs.

The term to "treat," as used herein, means reducing the frequency with which symptoms are experienced by a patient or subject or administering a composition to reduce the severity with which symptoms are experienced. An appropriate therapeutic amount in any individual case may be determined by one of ordinary skill in the art using routine experimentation.

The following abbreviations are used herein: DAPI, 4,6-diamidino-2-phenylindole; FT-IR, Fourier transform-infrared; GAPDH, glyceraldehyde 3-phosphate dehydrogenase; IgG, immunoglobulin G; mAb, monoclonal antibody; MAFMILHN, mucin1-aptamer functionalized miRNA-29b-loaded hybrid nanoparticle(s); miRNA, microRNA; MUC1, mucin 1.

Throughout this disclosure, various aspects of the present invention can be presented in a range format. It should be understood that the description in range format is merely for convenience and brevity and should not be construed as an inflexible limitation on the scope of the present invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions

In certain embodiments, the invention provides a protein-containing nanoparticle, wherein the core of the nanoparticle comprises at least one protein selected from the group consisting of a plasma protein, an IgG, a cytokine, an immunomodulator, an antigen, a hormone, and an enzyme, wherein the at least one protein is in a neutral state in the nanoparticle, wherein the nanoparticle is surrounded by a layer comprising a stealth polymer, wherein the at least one protein is conjugated with at least one cell surface receptor ligand, wherein at least a fraction of the ligand is displayed on the outer surface of the surrounding layer of the nanoparticle.

In certain embodiments, compositions of the invention are prepared using a method that comprises providing a solution comprising a protein of interest, and optionally at least one therapeutic agent, and titrating the solution to about the isoelectric point of the protein, thereby forming a precipitate comprising the protein nanoparticle, wherein the protein nanoparticle comprises at least a fraction of the protein (and at least a fraction of the therapeutic agent, if the at least one therapeutic agent is present in the solution). The protein nanoparticle is optionally purified; in a non-limiting example, the protein nanoparticle is washed with a solvent, such as but not limited to water. The protein nanoparticle is then resuspended in a solution comprising a stealth polymer, wherein the concentration of the stealth polymer in the solution ranges from about 0.1% to about 20,000% of the CMC of the stealth polymer, and optionally at least one therapeutic agent. The resulting stealth polymer-containing protein nanoparticle can then be purified and/or isolated from the solution. Optionally, a cell surface receptor ligand is present in the protein nanoparticle and/or the stealth polymer-containing protein nanoparticle.

In certain embodiments, the protein comprises a plasma protein, hormone, immunomodulator, cytokine, interferon, interleukin, or enzyme. In other embodiments, the protein comprises an antibody. In yet other embodiments, the protein comprises an immunoglobulin. In yet other embodiments, the immunoglobulin comprises IgA, IgD, IgE, IgG or IgM. In yet other embodiments, the immunoglobulin comprises IgG.

In certain embodiments, the stealth polymer comprises an alkyl polyethylene oxide. In other embodiments, the stealth polymer comprises an alkylphenol polyethylene oxide. In yet other embodiments, the stealth polymer comprises a copolymer of polyethylene oxide and polypropylene oxide. In yet other embodiments, the non-ionic surfactant comprises an alkyl polyglucoside. In yet other embodiments, the non-ionic surfactant comprises a fatty alcohol. In yet other embodiments, the non-ionic surfactant comprises a cocamide MEA. In yet other embodiments, the non-ionic surfactant comprises a cocamide DEA. In yet other embodiments, the stealth polymer comprises one or more of the polymers recited elsewhere herein.

In certain embodiments, the alkyl polyethylene oxide comprises diethylene glycol hexadecyl ether. In other embodiments, the alkyl polyethylene oxide comprises polyethylene glycol oleyl ether. In yet other embodiments, the alkyl polyethylene oxide comprises diethylene glycol octadecyl ether. In yet other embodiments, the alkyl polyethylene oxide comprises polyoxyethylene stearyl ether. In yet other embodiments, the alkyl polyethylene oxide comprises polyethylene glycol hexadecyl (cetyl) ether. In yet other embodiments, the alkyl polyethylene oxide comprises polyethylene glycol dodecyl (lauryl) ether. In yet other embodiments, the alkyl polyethylene oxide comprises decaethylene glycol oleyl ether. In yet other embodiments, the alkyl polyethylene oxide comprises polyethylene glycol octadecyl ether. In yet other embodiments, the alkyl polyethylene oxide comprises polyethylene glycol octadecyl ether. In yet other embodiments, the alkyl polyethylene oxide comprises one or more of the polymers recited elsewhere herein.

In certain embodiments, the average diameter of the at least one protein nanoparticle ranges from about 1 nm to about 1,000 nm. In other embodiments, the average diameter of the at least one protein nanoparticle ranges from about 10 nm to about 900 nm. In yet other embodiments, the average diameter of the at least one protein nanoparticle ranges from about 300 nm to about 600 nm. In yet other embodiments, the average diameter of the at least one protein nanoparticle ranges from about 250 nm to about 700 nm. In yet other embodiments, the average diameter of the at least one protein nanoparticle ranges from about 10 nm to about 120 nm. In yet other embodiments, the average diameter of the at least one protein nanoparticle ranges from about 20 nm to about 120 nm. In yet other embodiments, the average diameter of the at least one protein nanoparticle ranges from about 40 nm to about 120 nm. In yet other embodiments, the average diameter of the at least one protein nanoparticle ranges from about 60 nm to about 120 nm. In yet other embodiments, the average diameter of the at least one protein nanoparticle ranges from about 80 nm to about 120 nm. In yet other embodiments, the average diameter of the at least one protein nanoparticle ranges from about 100 nm to about 120 nm.

In certain embodiments, the concentration of the stealth polymer in the solution ranges from about 0.1% to about 20,000% of the CMC of the stealth polymer. In other embodiments, the concentration of the stealth polymer in the solution ranges from about 1% to about 100% of the CMC of the stealth polymer. In yet other embodiments, the concentration of the stealth polymer in the solution ranges from about 10% to about 100% of the CMC of the stealth polymer. In yet other embodiments, the concentration of the stealth polymer in the solution ranges from about 100% to about 20,000% of the CMC of the stealth polymer. In yet other embodiments, the concentration of the stealth polymer in the solution ranges from about 300% to about 10,000% of the CMC of the stealth polymer. In yet other embodiments, the concentration of the stealth polymer in the solution ranges from about 300% to about 5,000% of the CMC of the stealth polymer. In yet other embodiments, the composition further comprises a pharmaceutically acceptable carrier.

In certain embodiments of the present invention, the antibody comprises a monoclonal antibody. In other embodiments, the monoclonal antibody comprises bevacizumab, anatumomab, benralizumab, enokizumab, mitumomab, oxelumab, palivizumab or any combinations thereof.

Surfactants

Non-limiting examples of stealth polymers useful within the compositions and methods of the present invention are alkyl polyethylene oxide (such as, but not limited to, diethylene glycol hexadecyl ether, polyethylene glycol oleyl ether, diethylene glycol octadecyl ether, polyoxyethylene stearyl ether, polyethylene glycol hexadecyl (cetyl) ether, polyethylene glycol dodecyl (lauryl) ether, decaethylene glycol oleyl ether, polyethylene glycol octadecyl ether, and polyethylene glycol octadecyl ether), alkylphenol polyethylene oxide, copolymers of polyethylene oxide and polypropylene oxide (known as poloxamers or poloxamines), alkyl polyglucosides (including octyl glucoside and decyl maltoside), fatty alcohols (including cetyl alcohol and oleyl alcohol), cocamide MEA, and cocamide DEA.

Ligands

In certain embodiments, the nanoparticles of the present invention further comprise at least one cell surface receptor ligand. In certain embodiments, the ligands allow for the nanoparticles of the present invention to recognize and bind to a cell that displays such cell surface receptor.

Non-limiting examples of ligands contemplated within the invention include ligands that bind to at least one of the following receptors: neurotensin receptor-1, human epidermal growth factor receptor-2 (HER-2), folate receptor, insulin-like growth (IGF) receptor, and/or epidermal growth factor receptor (EGFR).

Non-limiting examples of ligands contemplated within the invention include anti-NTSR1-mAb or SR-48692 (also known as 2-[[[1-(7-chloro-4-quinolinyl)-5-(2,6-dimethoxyphenyl)-1H-pyrazol-3-yl]carbonyl]amino]-tricyclo [3.3.1.13,7]decane-2-carboxylic acid), which bind to neurotensin receptor-1; trastuzumab, which binds to HER-2; folic acid (also known as (2S)-2-[[4-[(2-amino-4-oxo-1H-pteridin-6-yl)methylamino]benzoyl]amino] pentanedioic acid, N-(4-{[(2-amino-4-oxo-1,4-dihydropteridin-6-yl)methyl] amino}benzoyl)-L-glutamic acid; pteroyl-L-glutamic acid; Vitamin B9; or folacin), which binds to the folate receptor; anti-IGF-mAb (such as MK-0646, MA5-12247, AVE1642, figitumumab, or IMC-A12), which binds to the IGF receptor; and gefinitib, erlotinib, panitumumab, cetuximab, zalutumumab, nimotuzumab or matuzumab, which bind to the EGFR receptor.

Antibodies

Antibodies are useful within the compositions and methods of the present invention. In certain embodiments, the antibody comprises IgG, bevacizumab, anatumomab, benralizumab, enokizumab, mitumomab, oxelumab, palivizumab and any combinations thereof within the methods of the present invention. In other embodiments, the antibody is human or humanized. In yet other embodiments, the antibody comprises an antibody selected from a polyclonal antibody, a monoclonal antibody, a humanized antibody, a synthetic antibody, a heavy chain antibody, a human antibody, and a biologically active fragment of an antibody.

Non-limiting examples of antibodies useful within the compositions and methods of the present invention include:

bevacizumab (AVASTIN®): humanized monoclonal antibody that inhibits vascular endothelial growth factor A (VEGF-A) and is used to treat cancers such as colon cancer, rectum cancer, lung cancer, glioblastoma, and renal cell cancer (Los et al., 2007, The Oncologist 12(4):443-50);

anatumomab mafenatox: a mouse monoclonal antibody for the treatment non-small cell lung cancer; a fusion protein of a Fab fragment with an enterotoxin ("mafenatox") of S. aureus;

benralizumab: a monoclonal antibody for the treatment of asthma, and directed against the alpha-chain of the interleukin-5 receptor (CD125) (Catley, 2010, IDrugs: Invest. Drugs J. 13 (9): 601-604);

enokizumab: a humanized monoclonal antibody designed for the treatment of asthma;

mitumomab (BEC-2): a mouse monoclonal antibody investigated for the treatment of small cell lung carcinoma;

oxelumab: human monoclonal antibody designed for the treatment of asthma; and, palivizumab (SYNAGIS®): a monoclonal antibody used in the prevention of respiratory syncytial virus (RSV) infections; a humanized monoclonal antibody (IgG) directed against an epitope in the A antigenic site of the F protein of RSV.

It will be appreciated by one skilled in the art that an antibody comprises any immunoglobulin molecule, whether derived from natural sources or from recombinant sources, which is able to specifically bind to an epitope present on a target molecule.

In one aspect of the present invention, the target molecule is directly neutralized by an antibody that specifically binds to an epitope on the target molecule. In another aspect of the present invention, the effects of the target molecule are blocked by an antibody that specifically binds to an epitope on a downstream effector. In still another aspect of the present invention, the effects of the target molecule are blocked by an antibody that binds to an epitope of an upstream regulator of the target molecule.

When the antibody to the target molecule used in the compositions and methods of the present invention is a polyclonal antibody (IgG), the antibody is generated by inoculating a suitable animal with a peptide comprising full length target protein, or a fragment thereof, an upstream regulator, or fragments thereof. These polypeptides, or fragments thereof, may be obtained by any methods known in the art, including chemical synthesis and biological synthesis, as described elsewhere herein. Antibodies produced in the inoculated animal that specifically bind to the target molecule, or fragments thereof, are then isolated from fluid obtained from the animal.

Antibodies may be generated in this manner in several non-human mammals such as, but not limited to goat, sheep, horse, camel, rabbit, and donkey. Methods for generating polyclonal antibodies are well known in the art and are described, for example in Harlow et al., 1998, In: Antibodies, A Laboratory Manual, Cold Spring Harbor, N.Y.

Monoclonal antibodies directed against a full length target molecule, or fragments thereof, may be prepared using any well-known monoclonal antibody preparation procedures, such as those described, for example, in Harlow et al. (1998, In: Antibodies, A Laboratory Manual, Cold Spring Harbor, N.Y.) and in Tuszynski et al. (1988, Blood, 72:109-115). Human monoclonal antibodies may be prepared by the method described in U.S. Patent Publication No. 2003/0224490. Monoclonal antibodies directed against an antigen are generated from mice immunized with the antigen using standard procedures as referenced herein. Nucleic acid encoding the monoclonal antibody obtained using the procedures described herein may be cloned and sequenced using technology which is available in the art, and is described, for example, in Wright et al., 1992, Critical Rev. Immunol. 12(3,4):125-168, and the references cited therein.

When the antibody used in the methods of the present invention is a biologically active antibody fragment or a synthetic antibody corresponding to antibody to a full length target molecule, or fragments thereof, the antibody is prepared as follows: a nucleic acid encoding the desired antibody or fragment thereof is cloned into a suitable vector. The vector is transfected into cells suitable for the generation of large quantities of the antibody or fragment thereof. DNA encoding the desired antibody is then expressed in the cell thereby producing the antibody. The nucleic acid encoding the desired peptide may be cloned and sequenced using technology available in the art, and described, for example, in Wright et al., 1992, Critical Rev. in Immunol. 12(3,4): 125-168 and the references cited therein. Alternatively, quantities of the desired antibody or fragment thereof may also be synthesized using chemical synthesis technology. If the amino acid sequence of the antibody is known, the desired antibody can be chemically synthesized using methods known in the art as described elsewhere herein.

The present invention also includes the use of humanized antibodies specifically reactive with an epitope present on a target molecule. These antibodies are capable of binding to the target molecule. The humanized antibodies useful in the invention have a human framework and have one or more complementarity determining regions (CDRs) from an antibody, typically a mouse antibody, specifically reactive with a targeted cell surface molecule.

When the antibody used in the invention is humanized, the antibody can be generated as described in Queen et al. (U.S. Pat. No. 6,180,370), Wright et al., 1992, Critical Rev. Immunol. 12(3,4):125-168, and in the references cited therein, or in Gu et al., 1997, Thrombosis & Hematocyst 77(4):755-759, or using other methods of generating a humanized antibody known in the art. The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, attached to DNA segments encoding acceptor human framework regions. Generally speaking, the invention in the Queen patent has applicability toward the design of substantially any humanized immunoglobulin. Queen explains that the DNA segments typically include an expression control DNA sequence operably linked to humanized immunoglobulin coding sequences, including naturally-associated or heterologous promoter regions. The expression control sequences can be eukaryotic promoter systems in vectors capable of transforming or transfecting eukaryotic host cells, or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

Human constant region (CDR) DNA sequences from a variety of human cells can be isolated in accordance with well-known procedures. Preferably, the human constant region DNA sequences are isolated from immortalized B-cells as described in International Patent Application Publication No. WO 198702671. CDRs useful in producing the antibodies of the present invention may be similarly derived from DNA encoding monoclonal antibodies capable of binding to the target molecule. Such humanized antibodies may be generated using well-known methods in any convenient mammalian source capable of producing antibodies, including, but not limited to, mice, rats, camels, llamas, rabbits, or other vertebrates. Suitable cells for constant region and framework DNA sequences and host cells in which the antibodies are expressed and secreted, can be obtained from a number of sources, such as the American Type Culture Collection, Manassas, Va.

One of skill in the art will further appreciate that the present invention encompasses the use of antibodies derived from camelid species. That is, the present invention includes, but is not limited to, the use of antibodies derived from species of the camelid family. As is well known in the art, camelid antibodies differ from those of most other mammals in that they lack a light chain, and thus comprise only heavy chains with complete and diverse antigen binding capabilities (Hamers-Casterman et al., 1993, Nature, 363:446-448). Such heavy-chain antibodies are useful in that they are smaller than conventional mammalian antibodies, they are more soluble than conventional antibodies, and further demonstrate an increased stability compared to some other antibodies. Camelid species include, but are not limited to Old World camelids, such as two-humped camels (*C. bactrianus*) and one humped camels (*C. dromedarius*). The camelid family further comprises New World camelids including, but not limited to llamas, alpacas, vicuna and guanaco. The production of polyclonal sera from camelid species is substantively similar to the production of polyclonal sera from other animals such as sheep, donkeys, goats, horses, mice, chickens, rats, and the like. The skilled artisan, when equipped with the present disclosure and the methods detailed herein, can prepare high-titers of antibodies from a camelid species. As an example, the production of antibodies in mammals is detailed in such references as Harlow et al., 1998, Antibodies: A Laboratory Manual, Cold Spring Harbor, N.Y.

$V_H$ proteins isolated from other sources, such as animals with heavy chain disease (Seligmann et al., 1979, Immunological Rev. 48:145-167, incorporated herein by reference in its entirety), are also useful in the compositions and methods of the present invention. The present invention further comprises variable heavy chain immunoglobulins produced from mice and other mammals, as detailed in Ward et al., 1989, Nature 341:544-546 (incorporated herein by reference in its entirety). Briefly, $V_H$ genes are isolated from mouse splenic preparations and expressed in *E. coli*. The present invention encompasses the use of such heavy chain immunoglobulins in the compositions and methods detailed herein.

Antibodies useful as target molecule depletors in the invention may also be obtained from phage antibody libraries. To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA that specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., 2001, Molecular Cloning: A Laboratory Manual, Cold Spring Harbor Laboratory Press, Cold Spring Harbor, N.Y.

Bacteriophage that encode the desired antibody may be engineered such that the protein is displayed on the surface thereof in such a manner that it is available for binding to its corresponding binding protein, e.g., the antigen against which the antibody is directed. Thus, when bacteriophage that express a specific antibody are incubated in the presence of a cell which expresses the corresponding antigen, the bacteriophage will bind to the cell. Bacteriophage that do not express the antibody will not bind to the cell. Such panning techniques are well known in the art and are described for example, in Wright et al., 1992, Critical Rev. Immunol. 12(3,4):125-168.

Processes such as those described above have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage that display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage that encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al., 1995, J. Mol. Biol. 248:97-105).

Once expressed, whole antibodies, dimers derived therefrom, individual light and heavy chains, or other forms of antibodies can be purified according to standard procedures known in the art. Such procedures include, but are not limited to, ammonium sulfate precipitation, the use of affinity columns, routine column chromatography, gel electrophoresis, and the like (see, generally, R. Scopes, "Protein Purification", Springer-Verlag, N.Y. (1982)). Substantially pure antibodies of at least about 90% to 95% homogeneity are contemplated; and antibodies having 98% to 99% or more homogeneity are also contemplated for pharmaceutical uses. Once purified, the antibodies may then be used to practice the method of the present invention, or to prepare a pharmaceutical composition useful in practicing the method of the present invention.

The antibodies of the present invention can be assayed for immunospecific binding by any method known in the art. The immunoassays that can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g, Current Protocols in Molecular Biology, (Ausubel et al., eds.), Greene Publishing Associates and Wiley-Interscience, New York (2002)). Exemplary immunoassays are described briefly below (but are not intended to be in any way limiting).

Therapeutic Agents

In certain embodiments, the nanoparticles of the present invention further comprise at least one therapeutic agent. The at least one therapeutic agent may be a therapeutic, prophylactic, and/or diagnostic agent. Any suitable therapeutic agent may be used within the compositions and methods of the present invention. Non-limiting examples of therapeutic agent contemplated within the invention include organic compounds, inorganic compounds, antibodies (such as any of the antibodies discussed elsewhere herein), hydrophobic or hydrophilic pharmacological drugs, radiopharmaceuticals, biologics, proteins, peptides, polysaccharides, nucleic acids, siRNA, miRNA, RNAi, short hairpin RNAs (shRNAs), antisense nucleic acids), ribozymes, dominant negative mutants, or other materials that can be incorporated into the nanoparticles using standard techniques and/or the methods described herein.

In certain embodiments, the nanoparticles comprise an interfering RNA that reduces translation of at least one cell protein and/or polypeptide in a cell of a subject, wherein the cell protein is associated with a disease or disorder in the subject. An interfering RNA can include a siRNA, a snRNA, and a microRNA. An siRNA polynucleotide is an RNA nucleic acid molecule that interferes with RNA activity that is generally considered to occur via a post-transcriptional gene silencing mechanism. An siRNA polynucleotide preferably comprises a double-stranded RNA (dsRNA) but is not intended to be so limited and may comprise a single-stranded RNA (see, e.g., Martinez et al., 2002 Cell 110:563-74). The siRNA polynucleotide included in the invention may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynucleotide or the like, typically in 5'- to 3'-phosphodiester linkage). Accordingly, it will be appreciated that certain exemplary sequences disclosed herein as DNA sequences capable of directing the transcription of the siRNA polynucleotides are also intended to describe the corresponding RNA sequences and their complements, given the well-established principles of complementary nucleotide base-pairing.

Contemplated siRNA polynucleotides comprise double-stranded polynucleotides of about 18-30 nucleotide base pairs, for example about 18, about 19, about 20, about 21, about 22, about 23, about 24, about 25, about 26, or about 27 base pairs, and in other embodiments about 19, about 20, about 21, about 22 or about 23 base pairs, or about 27 base pairs, whereby the use of "about" indicates that in certain embodiments and under certain conditions the processive cleavage steps that may give rise to functional siRNA polynucleotides that are capable of interfering with expression of a selected polypeptide may not be absolutely efficient. Hence, siRNA polynucleotides may include one or more siRNA polynucleotide molecules that may differ (e.g., by nucleotide insertion or deletion) in length by one, two, three, four or more base pairs as a consequence of the variability in processing, in biosynthesis, or in artificial synthesis of the siRNA. The siRNA polynucleotide of the present invention may also comprise a polynucleotide sequence that exhibits variability by differing (e.g., by nucleotide substitution, including transition or transversion) at one, two, three or four nucleotides from a particular sequence. These differences can occur at any of the nucleotide positions of a particular siRNA polynucleotide sequence, depending on the length of the molecule, whether situated in a sense or in an antisense strand of the double-stranded polynucleotide. The nucleotide difference may be found on one strand of a double-stranded polynucleotide, where the complementary nucleotide with which the substitute nucleotide would typically form hydrogen bond base pairing, may not necessarily be correspondingly substituted. In certain embodiments, the siRNA polynucleotides are homogeneous with respect to a specific nucleotide sequence.

It should be appreciated that the siRNAs of the present invention may effect silencing of the target polypeptide expression to different degrees. Selection of siRNAs are made therefrom based on the ability of a given siRNA to interfere with or modulate the expression of the target polypeptide. The methods for testing each siRNA and selection of suitable siRNAs for use in the present invention are fully known to those skilled in the art. It is appreciated by one skilled in the art that siRNAs are easily designed and manufactured. Further, effects of siRNA are typically transient in nature, which make them optimal for certain therapies where sustained inhibition is undesired. Another form of an interfering RNA, snRNA polynucleotides utilize the endogenous processing machinery of the cell and are often designed for high potency, sustainable effects, and fewer off-target effects (Rao et al., 2009, Adv Drug Deliv Rev, 61: 746-759). As would be understood by those skilled in the art, the present invention encompasses both siRNA and snRNA polynucleotides, which can be designed and delivered to inhibit one or more cell proteins.

One skilled in the art will appreciate that one way to decrease the mRNA and/or protein levels of a cell protein is by reducing or inhibiting expression of the nucleic acid encoding the cell protein. Thus, the level of the cell protein in a cell can also be decreased using a molecule or compound that inhibits or reduces gene expression such as, for example, an antisense molecule or a ribozyme.

In certain embodiments, the modulating sequence is an antisense nucleic acid sequence expressed by a plasmid vector. The antisense expressing vector is used to transfect a mammalian cell or the mammal itself, thereby causing reduced endogenous expression of a desired protein in the cell. However, the invention should not be construed to be limited to inhibiting expression of a protein by transfection of cells with antisense molecules. Rather, the invention encompasses other methods known in the art for inhibiting expression or activity of a protein in the cell including, but not limited to, the use of a ribozyme, the expression of a non-functional protein (i.e. dominant negative mutant) and use of an intracellular antibody.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

In another aspect of the present invention, the protein can be inhibited by way of inactivation and/or sequestration. As such, inhibiting the effects of a protein can be accomplished by using a dominant negative mutant. Alternatively an antibody specific for the desired protein, otherwise known as an antagonist to the protein, may be used. In certain embodiments, the antagonist is a protein and/or compound having the desirable property of interacting with a binding partner of the protein and thereby competing with the corresponding wild-type protein. In another embodiments, the antagonist is a protein and/or compound having the desirable property of interacting with the protein and thereby sequestering the protein.

Inhibition of one or more cell proteins can be accomplished using a modified nucleic acid molecule, such as a small interfering RNA (siRNA), short hairpin RNA (snRNA), a microRNA, an antisense nucleic acid, a ribozyme, an expression vector encoding a dominant negative mutant, and the likes. The methods of modifying nucleic acid molecules are known in the art. For example, a number of specific siRNA polynucleotide sequences useful for interfering with target polypeptide expression are known in the art. siRNA polynucleotides may generally be prepared by any method known in the art, including, for example, solid phase chemical synthesis. Modifications in a polynucleotide sequence may also be introduced using standard mutagenesis techniques, such as oligonucleotide-directed site-specific mutagenesis. Further, siRNAs may be chemically modified or conjugated with other molecules to improve their stability and/or delivery properties. Included as one aspect of the present invention are siRNAs as described herein, wherein one or more ribose sugars has been removed therefrom.

Alternatively, siRNA polynucleotide molecules may be generated by in vitro or in vivo transcription of suitable DNA sequences (e.g., polynucleotide sequences encoding a target polypeptide, or a desired portion thereof), provided that the DNA is incorporated into a vector with a suitable RNA polymerase promoter (such as for example, T7, U6, H1, or SP6 although other promoters may be equally useful). In addition, an siRNA polynucleotide may be administered to a mammal, as may be a DNA sequence (e.g., a recombinant nucleic acid construct as provided herein) that supports transcription (and optionally appropriate processing steps) such that a desired siRNA is generated in vivo.

In certain embodiments, an siRNA polynucleotide, wherein the siRNA polynucleotide is capable of interfering with expression of a target polypeptide can be used to generate a silenced cell. Any siRNA polynucleotide that, when contacted with a biological source for a period of time, results in a significant decrease in the expression of the target polypeptide is included in the invention. Preferably the decrease is greater than about 10%, more preferably greater than about 20%, more preferably greater than about 30%, more preferably greater than about 40%, about 50%, about 60%, about 70%, about 75%, about 80%, about 85%, about 90%, about 95% or about 98% relative to the expression level of the target polypeptide detected in the absence of the siRNA. Preferably, the presence of the siRNA polynucleotide in a cell does not result in or cause any undesired toxic effects, for example, apoptosis or death of a cell in which apoptosis is not a desired effect of RNA interference.

Any polynucleotide of the present invention may be further modified to increase its stability in vivo. Possible modifications include, but are not limited to, the addition of flanking sequences at the 5' and/or 3' ends; the use of phosphorothioate or 2'-O-methyl rather than phosphodiester linkages in the backbone; and/or the inclusion of non-traditional bases such as inosine, queosine, and wybutosine and the like, as well as acetyl-methyl-, thio- and other modified forms of adenine, cytidine, guanine, thymine, and uridine.

Methods

The invention provides a method of preparing at least one stealth polymer-containing protein nanoparticle. In certain embodiments, the method comprises adjusting the pH of a first solution comprising a protein to about the isoelectric point of the protein, thereby forming a first protein nanoparticle, which comprises at least a fraction of the protein. In other embodiments, if the protein in the first protein nanoparticle is not conjugated to at least one cell surface receptor ligand, the protein in the first protein nanoparticle is further conjugated with the at least one cell surface receptor. In yet other embodiments, the method comprises contacting the first protein nanoparticle with a second solution comprising a stealth polymer, wherein the concentration of the stealth polymer in the second solution ranges from about 0.1% to about 20,000% of the CMC of the stealth polymer. In yet other embodiments, the at least one stealth polymer-containing protein nanoparticle is prepared.

The invention further provides a method of treating, ameliorating or preventing a disease or disorder in a subject in need thereof. In certain embodiments, the method comprises administering to the subject a pharmaceutically effective amount of a composition of the invention.

In certain embodiments, the at least one stealth polymer-containing protein nanoparticle is further purified to remove protein or stealth polymer that is not associated with the at least one stealth polymer-containing protein nanoparticle, thereby generating a composition comprising the at least one stealth polymer-containing protein nanoparticle.

In certain embodiments, the composition comprising at least one stealth polymer-containing protein nanoparticle is further lyophilized.

In certain embodiments, the protein comprises at least one selected from the group consisting of a plasma protein, hormone, immunomodulator, cytokine, interferon, interleukin, and enzyme. In other embodiments, the protein comprises an antibody. In yet other embodiments, the antibody comprises IgA, IgD, IgE, IgG, and/or IgM.

In certain embodiments, the first solution further comprises at least one therapeutic agent, and wherein the first protein nanoparticle comprises at least a fraction of the at least one therapeutic agent. In other embodiments, the at least therapeutic agent is selected from the group consisting of an organic compound, inorganic compound, antibody, pharmacological drug, radiopharmaceutical, protein, peptide, polysaccharide, nucleic acid, siRNA, RNAi, short hairpin RNA, antisense nucleic acid, ribozyme and dominant negative mutant. In yet other embodiments, the at least therapeutic agent comprises a siRNA or miRNA.

In certain embodiments, the protein in the protein nanoparticle is conjugated non-covalently and/or covalently to the at least one cell surface receptor ligand. In other embodiments, the at least one cell surface receptor ligand binds to at least one selected from the group consisting of neurotensin receptor-1, human epidermal growth factor receptor-2 (HER-2), folate receptor, insulin-like growth receptor (IGF), and epidermal growth factor receptor (EGFR). In yet other embodiments, the stealth polymer comprises at least one selected from the group consisting of alkyl polyethylene oxide, alkylphenol polyethylene oxide, copolymer of polyethylene oxide and polypropylene oxide, alkyl polyglucoside, fatty alcohol, cocamide MEA, and cocamide DEA. In yet other embodiments, the alkyl polyethylene oxide comprises at least one selected from the group consisting of diethylene glycol hexadecyl ether, polyethylene glycol oleyl ether, diethylene glycol octadecyl ether, polyoxyethylene stearyl ether, polyethylene glycol hexadecyl (cetyl) ether, polyethylene glycol dodecyl (lauryl) ether, decaethylene glycol oleyl ether, polyethylene glycol octadecyl ether, and polyethylene glycol octadecyl ether.

In certain embodiments, the average diameter of the at least one stealth polymer-containing nanoparticle ranges from about 1 nm to about 1,000 nm. In other embodiments, the concentration of the stealth polymer in the second solution ranges from about 100% to about 20,000% of the CMC of the stealth polymer. In yet other embodiments, the at least one stealth polymer-containing protein nanoparticle is formulated with a pharmaceutically acceptable carrier.

In certain embodiments, the composition is administered to the subject by an intrapulmonary, intrabronchial, inhalational, intranasal, intratracheal, intravenous, intramuscular, subcutaneous, topical, transdermal, oral, buccal, rectal, pleural, peritoneal, vaginal, epidural, otic, intraocular, or intrathecal route. In other embodiments, the composition is administered to the subject by an intrapulmonary, intrabronchial, inhalational, intranasal, intratracheal, intravenous, intramuscular, subcutaneous or topical route.

In certain embodiments, the composition further comprises a pharmaceutically acceptable carrier.

In certain embodiments, the protein comprises IgG and the nanoparticle further comprises a therapeutic agent comprising a siRNA or a miRNA.

In certain embodiments, the stealth polymer comprises a copolymer of polyethylene oxide and polypropylene oxide.

In certain embodiments, the disease or disorder is selected from the group consisting of colon cancer, rectum cancer, lung cancer, glioblastoma, renal cell cancer, non-small cell lung cancer, small cell lung cancer, asthma, respiratory syncytial virus (RSV) infection, and any combinations thereof. In other embodiments, the disease or disorder comprises a cancer comprising a KRAS mutation.

In certain embodiments, the subject is a mammal. In other embodiments, the mammal is human.

Pharmaceutical Compositions and Formulations

The invention also encompasses the use of pharmaceutical compositions of at least one composition of the present invention or a salt thereof to practice the methods of the present invention.

Such a pharmaceutical composition may consist of at least one composition of the present invention or a salt thereof, in a form suitable for administration to a subject, or the pharmaceutical composition may comprise at least one composition of the present invention or a salt thereof, and one or more pharmaceutically acceptable carriers, one or more additional ingredients, or some combination of these. The at least one composition of the present invention may be present in the pharmaceutical composition in the form of a physiologically acceptable salt, such as in combination with a physiologically acceptable cation or anion, as is well known in the art.

In certain embodiments, the pharmaceutical compositions useful for practicing the method of the present invention may be administered to deliver a API dose of between 1 ng/kg/day and 100 mg/kg/day, between 1 ng/kg/day and 500 mg/kg/day, or between 1 pg/kg/day and 10 ng/kg/day.

The relative amounts of the active ingredient, the pharmaceutically acceptable carrier, and any additional ingredients in a pharmaceutical composition of the present invention will vary, depending upon the identity, size, and condition of the subject treated and further depending upon the route by which the composition is to be administered.

Pharmaceutical compositions that are useful in the methods of the present invention may be suitably developed for inhalational, pulmonary, intranasal, intratracheal, intravenous, intramuscular, subcutaneous, topical, or another route of administration. Other contemplated formulations include projected nanoparticles, containing the active ingredient, and immunologically-based formulations. The route(s) of administration are readily apparent to the skilled artisan and depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose. The unit dosage form may also be for extended duration administration, such as once weekly or once monthly, depending on the efficacy of the protein formulation and the disease.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the present invention is contemplated include, but are not limited to, humans and other primates, mammals including commercially relevant mammals such as cattle, pigs, horses, sheep, cats, and dogs.

In certain embodiments, the compositions of the present invention are formulated using one or more pharmaceutically acceptable excipients or carriers. In certain embodiments, the pharmaceutical compositions of the present invention comprise a therapeutically effective amount of at least one composition of the present invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of stealth polymers. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition.

Formulations may be employed in admixtures with conventional excipients, i.e., pharmaceutically acceptable organic or inorganic carrier substances suitable for nasal, inhalational, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents. As used herein, "additional ingredients" include, but are not limited to, one or more ingredients that may be used as a pharmaceutical carrier.

The composition of the present invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, and combinations thereof. A contemplated preservative is a combination of about 0.5% to 2.0% benzyl alcohol and 0.05% to 0.5% sorbic acid.

The composition preferably includes an antioxidant and a chelating agent that inhibit the degradation of the compound. Contemplated antioxidants for some compounds are butylated hydroxytoluene (BHT), butylated hydroxyanisole (BHA), alpha-tocopherol (vitamin E) and ascorbic acid in the range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Contemplated chelating agents include edetate salts (e.g. disodium ethylenediaminetetracetic acid (EDTA)) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are contemplated antioxidant and chelating agent respectively for some compounds, other suitable and equivalent antioxidants and chelating agents may be substituted therefore as would be known to those skilled in the art.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Administration/Dosing

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

When used in vivo, the compositions of the present invention are preferably administered as a pharmaceutical composition, comprising a mixture, and a pharmaceutically acceptable carrier. The compositions of the present invention may be present in a pharmaceutical composition in an amount from 0.001 to 99.9 wt %, more preferably from about 0.01 to 99 wt %, and even more preferably from 0.1 to 95 wt %.

Administration of the compositions of the present invention to a patient, preferably a mammal, more preferably a human, may be carried out using known procedures, at dosages and for periods of time effective to treat a disease or disorder in the patient. An effective amount of the therapeutic compound necessary to achieve a therapeutic effect may vary according to factors such as the activity of the particular composition employed; the time of administration; the rate of excretion of the composition; the duration of the treatment; other drugs, compounds or materials used in combination with the composition; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the present invention is from about 0.01 µg/kg and 10 mg/kg of body weight/per day. One of ordinary skill in the art would be able to study the relevant factors and make the determination regarding the effective amount of the therapeutic composition without undue experimentation.

The composition can be administered to an animal as frequently as several times daily, or it may be administered less frequently, such as once a day, once a week, once every two weeks, once a month, or even less frequently, such as once every several months or even once a year or less. It is understood that the amount of composition dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the present invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the present invention are dictated by and directly dependent on (a) the unique characteristics of the therapeutic composition and the particular therapeutic effect to be achieved, and (b) the limitations inherent in the art of compounding/formulating such a therapeutic composition for the treatment of diseases or disorders in a patient.

In certain embodiments, the compositions of the present invention are administered to the patient in dosages that range from one to five times per day or more. In other embodiments, the compositions of the present invention are administered to the patient in range of dosages that include, but are not limited to, once every day, every two, days, every three days to once a week, and once every two weeks. It will be readily apparent to one skilled in the art that the frequency of administration of the various combination compositions of the present invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compositions of the present invention for administration may be in the range of from about 1 µg to about 1,000 mg, about 2 µg to about 500 mg, about 4 µg to about 250 mg, about 6 µg to about 200 mg, about 8 µg to about 100 mg, about 10 µg to about 50 mg, about 20 µg to about 25 mg, about 40 µg to about 10 mg, about 50 µg to about 5 mg, about 100 µg to about 1 mg, and any and all whole or partial increments thereinbetween.

In some embodiments, the dose of a composition of the present invention is from about 0.5 µg and about 2,000 mg. In some embodiments, a dose of a composition described herein is less than about 2,000 mg, or less than about 1,000 mg, or less than about 500 mg, or less than about 250 mg, or less than about 100 mg, or less than about 50 mg, or less than about 25 mg, or less than about 10 mg, or less than about 5 mg, or less than about 1 mg, and any and all whole or partial increments thereof.

In certain embodiments, the present invention is directed to a packaged pharmaceutical composition comprising a container holding a therapeutically effective amount of a composition of the present invention, alone or in combination with a second pharmaceutical agent; and instructions for using the composition to treat, prevent, or reduce one or more symptoms of a disorder or disease in a patient.

The term "container" includes any receptacle for holding the pharmaceutical composition. For example, in certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a breathing disorder in a patient.

Routes of Administration

Routes of administration of any of the compositions of the present invention include intrapulmonary, intrabronchial, inhalational, intranasal, intratracheal, intravenous, intramuscular, subcutaneous, topical, transdermal, oral, buccal, rectal, pleural, peritoneal, vaginal, epidural, otic, intraocular, or intrathecal administration.

Suitable compositions and dosage forms include, for example, suspensions, granules, beads, powders, pellets, and liquid sprays for nasal administration, dry powder or aerosolized formulations for inhalation, and the like. It should be understood that the formulations and compositions that would be useful in the present invention are not limited to the particular formulations and compositions that are described herein. For example, formulations may comprise a powder or an aerosolized or atomized solution or suspension comprising the active ingredient. Such powdered, aerosolized, or aerosolized formulations may further comprise one or more of the additional ingredients described herein. The examples of formulations described herein are not exhaustive and it is understood that the invention includes additional modifications of these and other formulations not described herein, but which are known to those of skill in the art.

Controlled Release Formulations and Drug Delivery Systems

In certain embodiments, the formulations of the present invention can be, but are not limited to, short-term release or rapid-offset release, as well as controlled release, for example, sustained release, delayed release and pulsatile release formulations.

The term short-term or rapid-offset release is used in its conventional sense to refer to a drug formulation that provides for release of the drug immediately after drug administration.

As used herein, short-term or rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments there between after drug administration after drug administration.

The term sustained release is used in its conventional sense to refer to a drug formulation that provides for gradual release of a drug over an extended period of time, and that may, although not necessarily, result in substantially constant blood levels of a drug over an extended time period. The period of time can be as long as a month or more and should be longer than the time required for the release of the same amount of agent administered in bolus form.

For sustained release, the compounds can be formulated with a suitable polymer or hydrophobic material that provides sustained release properties to the compounds. As such, the compounds of the present invention can be administered in the form of microparticles for example, by injection or in the form of wafers or discs by implantation.

In certain embodiments of the present invention, the compositions of the present invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

In certain embodiments of the present invention, the compositions of the present invention are administered to a subject, alone or in combination with another pharmaceutical agent, using a delayed release formulation.

The term pulsatile release is used herein in its conventional sense to refer to a drug formulation that provides release of the drug in such a way as to produce pulsed plasma profiles of the drug after drug administration.

In certain embodiments of the present invention, the compositions of the present invention are administered to a subject, alone or in combination with another pharmaceutical agent, using a pulsatile release formulation.

Kits

The invention also includes a kit comprising a composition of the present invention and an instructional material that describes administering the composition to a mammal. As used herein, an "instructional material" includes a publication, a recording, a diagram, or any other medium of expression that can be used to communicate the usefulness of the composition of the present invention in the kit for effecting alleviation of the various diseases or disorders recited herein.

Optionally, or alternatively, the instructional material may describe one or more methods of alleviating the diseases or disorders in a cell or a tissue of a mammal. The instructional material of the kit may, for example, be affixed to a container that contains the invention or be shipped together with a container that contains the invention. Alternatively, the instructional material may be shipped separately from the container with the intention that the instructional material and the compound be used cooperatively by the recipient.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Experimental Details

Materials

Human IgG was purchased from Equitech-Bio Inc. (Kerrville, Tex., USA). Poloxamer-188, RNase-free water, 4,6-diamidino-2-phenylindole (DAPI), HCl, and fetal bovine serum (FBS) were obtained from Thermo Fisher Scientific (Waltham, Mass., USA).

Aptamer against MUC1 (5'-GCA GTT GAT CCT TTG GAT ACC CTG G-3'; SEQ ID NO:1) was designed and purchased from GE Healthcare Bio-Sciences Corp. (Piscataway, N.J., USA). A C12 spacer was attached to the aptamer at the 3'-end to form the following sequence: 5'-GCA GTT GAT CCT TTG GAT ACC CTG G-$C_{12}H_{25}$-3' (SEQ ID NO:1—$C_{12}H_{25}$). One aptamer was modified with 3'-$NH_2$ and 5'-FITC, whereas the other was only modified with 3'-$NH_2$. The aptamers contained a 12-carbon spacer.

siGLO-Green (6-FAM-labeled) was obtained from GE Healthcare Bio-Sciences Corp. HCl was obtained from Thermo Fisher Scientific. MiRIDIAN mimic with miR-29b and miRIDIAN mimic NC were obtained from GE Healthcare Bio-Sciences Corp. Pierce RIPA lysis buffer was purchased from Thermo Fisher Scientific. Rabbit antihuman DNMT3B and rabbit antihuman MCL1 antibody were obtained from Thermo Fisher Scientific. Mouse antihuman β-tubulin antibody was purchased from Sigma-Aldrich (St Louis, Mo., USA).

Cell Culture

Adenocarcinoma cell line A549 and normal lung fibroblast cell line MRC-5 were obtained from American Type Culture Collection (Rockville, Md., USA). A549 cell was originally derived from a 58-year-old male Caucasian, while MRC-5 was originally derived from a 14-week gestation male Caucasian. A549 cells were maintained in F12 K medium supplemented with 10% FBS and 1% antibiotics. MRC-5 was maintained in Eagle's Minimum Essential Medium supplemented with 10% FBS. Both cells were kept in a humidified air atmosphere with 5% carbon dioxide.

Preparation of Nanoparticles

Human IgG was diluted in 0.01N HCl to make up IgG concentration of 1 mg/mL (i.e., 10 mg) in 10 mL of 0.01 N HCl. A total of 0.73 mg of miRNA-29b was then added. The mixture was stirred on a magnetic stirrer until all the components were fully dissolved. The mixture was titrated with 0.01 N NaOH up to a pH value close to 7. Nanoparticles were spontaneously formed at the pH value very close to 7. The nanoparticles were allowed to mix on the magnetic stirrer for about 10 minutes. The colloidal suspension was centrifuged using a microcentrifuge (Eppendorf centrifuge 5418) at 2,000 rpm for 5 minutes. The supernatant was either decanted or kept for the measurement of unencapsulated miRNA-29b to be used to calculate encapsulation efficiency and loading capacity. Nanoparticles were then rinsed three times with double distilled deionized water. Nanoparticles were subsequently suspended in 0.2% v/v poloxamer-188, with gentle shaking for 10 minutes in order to coat nanoparticles with poloxamer-188. Nanoparticles were centrifuged and the supernatant decanted before being rinsed thrice with double distilled deionized water. Particles were then loaded into a freeze dryer (Labconco Freeze Zone 4.6), and lyophilization was performed for 48 hours.

Conjugation of Aptamer to Prepared Nanoparticles

Figure 6:
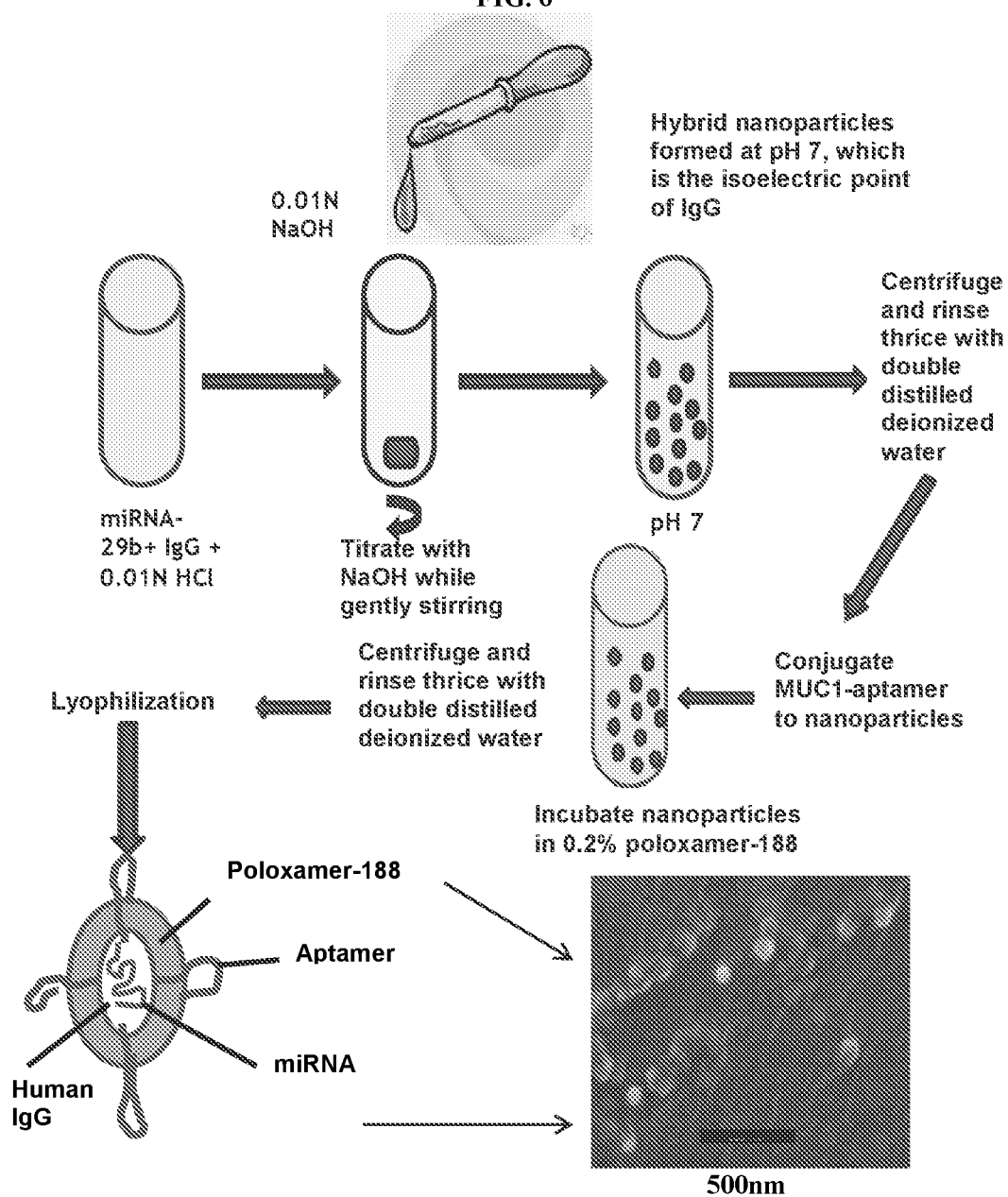
FIG. 6 illustrates preparation and characterization of mucin1-aptamer functionalized miRNA-29b-loaded hybrid nanoparticles (MAFMILHN). Schematic showing the procedure involved in the production of MAFMILHN.

A total of 50 μL of poloxamer-free nanoparticle suspension (10 μg/mL in DNase, RNase-free water) was mixed with 100 μL of 40 mM EDC and 100 μL of 10 mM NHS for 15 minutes at room temperature with gentle stirring. This helps to activate the carboxyl groups on nanoparticles for aptamer conjugation. A total of 50 μL of 1 μg/mL aptamer in DNase, RNAse-free water was then added to the nanoparticles and mixed gently for 2 hours at room temperature. Nanoparticles were subsequently centrifuged at 4,000 rpm and 10° C. for 5 minutes using 30 kDa cutoff centrifugal ultrafilters (EMD Millipore, Billerica, Mass., USA) to exclude unreacted EDC and NHS. Aptamer-functionalized nanoparticles were then suspended in 0.2% v/v poloxamer-188, with gentle shaking for 10 minutes in order to coat them with poloxamer-188. FIG. 6 illustrates a non-limiting sequence involved in the preparation of MAFMILHN.

Characterization of Nanoparticles

Particle size and surface charge (zeta potential) of the nanoparticles were measured using photon correlation spectroscopy (ZetaSizer Nano ZS; Malvern Instruments, Malvern, UK). Nanoparticles were dispersed in deionized water followed by sonication for about 5 minutes. A scattering angle (θ) of 173° was used to measure intensity autocorrelation. The Z-average and polydispersity index were recorded in triplicate. For zeta potential, samples were taken in a universal dip cell (Malvern Instruments) and the zeta potential recorded in triplicate.

The shape of nanoparticles was evaluated using scanning electron microscopy. Suspensions of nanoparticles were dropped on an aluminum stub and allowed to dry at room temperature. Samples were then coated with a thin layer of palladium. Coated samples were imaged using a Zeiss Supra 50 V system (Carl Zeiss Meditec AG, Jena, Germany).

Fourier Transform-Infrared Spectroscopy

A single-reflection-attenuated total reflectance with a diamond internal reflection crystal installed in an iS10 FT-IR spectrometer (Thermo Fisher Scientific) was used to obtain spectra from different samples of nanoparticles. Lyophilized powders were placed on the surface of the attenuated total reflectance crystal after background spectra had been collected. Spectra were collected after 64 scans at 4 cm-1 resolution. Data were analyzed using OMNIC software.

miRNA Release Study

Release of miRNA from MUC1 aptamer-functionalized hybrid nanoparticles was measured at pH values 5, 6.6, and 7.4. Nanoparticles (3 mg) were dispersed in 0.5 mL of a buffered solution in a tubular cellulose dialysis membrane secured tightly at both ends. This was then incubated at 37° C. in 5 mL buffered solution reservoirs while the reservoir was gently agitated. The amount of miRNA released at different time points was analyzed and quantified for percentage cumulative release using ion-pair HPLC.

Ion-Pair HPLC miRNA was quantitatively determined using a Waters 2695 separation module combined with a Waters 2998 photodiode array detector Alliance HPLC system (Waters, Milford, Mass., USA). Using a Clarity 3 μm Oligo-RP column (Phenomenex, Torrance, Calif., USA) with a column dimension of 50×2.0 mm, 1 μL of miRNA sample was injected into the HPLC using 20 mM triethylamine-acetic acid (pH 7) and 5%-12% acetonitrile, gradient elusion as mobile phase. A flow rate of 0.2 mL/min was used for analysis. UV detection was performed at 269 nm, and Empower Pro software was used to record chromatograms.

Isolation of miRNA-29b and Ion-Pair HPLC

Using Clarity OTX kit (Phenomenenex, CA) with Thermo Scientific HyperSep Vacuum Manifold (Thermo-Scientific, Rockwood, Tenn.), miRNA-29b was isolated from blood and tissues for ion-pair HPLC analysis according to manufacturer's instructions. Equal aliquots of Clarity OTX loading buffer was mixed with plasma samples which were then loaded on the solid Phase Extraction (SPE) cartridge. Equilibration of the SPE isolation cartridge (Clarity OTX 100 mg/3 mL: Phenomenex) was done after it was first wetted with methanol. Equilibration was done with Clarity equilibration buffer (10 mM phosphate pH 5.5). To isolate miRNA-29b from tissue samples, tissues were homogenized in 0.1 M Tris buffer, pH 8.0 and then mixed with equal amount of Lysis-loading buffer. Following sample loading, equilibration buffer was added to the cartridge to rinse twice. The cartridge was then rinsed with Clarity OTX wash buffer (10 mM phosphate pH 5.5/50% acetonitrile). MiRNA-29b was then eluted with 100 mM ammonium bicarbonate pH 8.0/40% acetonitrile/10% tetrahydrofuran. Samples were then concentrated to 100 µL with speed vacuum before ion-pair HPLC analysis.

Fluorescence Microscopy

A549 cells were seeded at a density of $2\times10^4$ in eight-well coated glass slides (Discovery Labware, Tewksbury, Mass., USA) followed by incubation for 48 hours. Cells were washed with PBS and incubated with either FITC-MUC1 aptamer-functionalized miRNA-29b-loaded hybrid nanoparticles or MUC1 aptamer-functionalized siGLO-FAM-loaded hybrid nanoparticles dispersed in the Opti-Mem medium at a concentration of 100 µg/mL for 2 hours or 4 hours. Cells were then washed twice with PBS, fixed using 2% paraformaldehyde, and incubated at room temperature for 20 minutes. Cells washed with PBS were then blocked with 5% BSA for 30 minutes at room temperature. Cells were stained with either Lysotracker-Red or AlexaFluoro-555-labeled wheat germ agglutinin (WGA-AF-555) before being stained with DAPI to visualize nucleus. Leica DMI 6000B fluorescence microscope (Leica Microsystems, Wetzlar, Germany) was then used to observe cells after being mounted.

Reverse Transcriptase Polymerase Chain Reaction

Qiagen RNAeasy kit (Qiagen, NV, Venlo, Netherlands) was used to isolate total RNA and Verzo cDNA kit (Thermo Fisher Scientific) was used for reverse transcription. Polymerase chain reaction (PCR) was carried out in 25 µL reaction mixtures. These reaction mixtures contained 1.0 µL of cDNA, 1x Qiagen buffer, 0.2 mM of dNTP mixture, 0.2 µM of each primer, and 1.5 U of HotStar Taq (Qiagen, Valencia, Calif., USA). One cycle reaction at 95° C. for 15 minutes was followed by 35 amplification cycles (94° C. for 1 minute, 66° C. for 1 minute, and 72° C. for 1 minute) for MUC1. For β-actin PCR, the same conditions except for the annealing temperature (59° C.) were used. Primer sequences of MUC1 are forward 5'-TCTCAAGCAGCCAGCGCCTGCCTG-3' (SEQ ID NO:2), and reverse 5'-TCCCCAGGTGGCAGCTGAACC-3' (SEQ ID NO:3). Primer sequences of β-actin are forward 5'-CCAAGGCCAACCGCGAGAAGAT-3' (SEQ ID NO:4), and reverse 5'-TTGCTCGAAGTCCAGGGCGA-3' (SEQ ID NO:5).

Flow Cytometry

Approximately 1 million cells per well (A549 and MRC-5) were seeded in a six-well plate and incubated for 48 hours. Cells were then treated with 100 µg/mL of siGLO-FAM-loaded equivalent nanoparticles resuspended in Opti-MEM medium and incubated for 4 hours. Corresponding cells were pretreated with five times excess of free MUC1 aptamer, 60 minutes prior to being treated with the MUC1 aptamer-functionalized siGLO-FAM-loaded hybrid nanoparticles. Cells were washed with PBS. The cells were then detached by trypsinization and centrifuged at 1,000 rpm for 5 minutes. The pellet was washed and resuspended in PBS. A 0.75 µm cell strainer was used to filter the cells before being analyzed by flow cytometry (BDFACS caliber) to prevent cell aggregates from blocking the tube lines of the instrument. A total of 10,000 cells were measured in each sample.

Terminal Deoxynucleotidyl Transferase dUTP Nick End Labeling (TUNEL) Analysis

TUNEL assay was performed with TACS 2TdT-Fluor in Situ Apoptosis Detection Kit (Trevigen, Gaithersburg, Md.) according to manufacturer's instruction. Lung tissue section slides were deparaffinised in xylene, 100%, 95%, 70% ethanol, followed by two changes of PBS. Samples were then digested with 50 µl of Cytonin solution for 30 min and washed with water and TdT Labelling Buffer. The slides were then covered with 50 µl of labelling reaction mix, which was then incubated for 60 min at 37° C. in a humidity chamber. Positive control was generated for comparison by incubating the slide with TACS-Nuclease (generating DNA breaks in every cell) at room temperature for 40 min, which was then followed by the labelling step. Stop Buffer was then used to halt the labelling reaction, samples washed in PBS and covered with 50 µl of Strep-Fluorescein Solution for 20 min. Slides were then washed with PBS, mounted and viewed under fluorescence microscope at 495 nm.

Cell Death Detection ELISA

Cell death detection ELISA was carried out according to manufacturer's instructions (Hoffman-La Roche Ltd., Basel, Switzerland). Briefly, A549 cells were seeded at a density of $2\times10^4$/well for 24 hours. Next day they were treated with MUC1 aptamer-functionalized miR-29b-loaded hybrid nanoparticles, MUC1 aptamer-functionalized negative control miRNA-loaded hybrid nanoparticles, and miR-29b in Lipofectamine 2000 Transfection Agent (Ambion, Austin, Tex., USA) in Opti-MEM medium. Cells were washed in PBS and lysed in 200 µL/well of incubation buffer for 30 minutes at room temperature. The lysates were centrifuged at 4,000×g for 10 minutes. Supernatant was used right away in the experiment. Plastic wells of the ELISA kit were incubated with coating solution (containing antihistone antibodies) overnight at 4° C. Next day it was substituted by incubation buffer for 30 minutes and washed three times with washing solution. A total of 100 µL of homogenate was placed into the wells and incubated for 90 minutes at room temperature with mild shaking. It was washed three times and incubated with conjugate solution containing anti-DNA peroxidase antibodies for 90 minutes. Wells were washed three times and exposed to ABTS substrate for 30 minutes until the color developed. Absorption values were read using a BioTek Epoch Microplate Spectrophotometer (BioTek Instruments Inc., Winooski, Vt., USA) with Gen5 1.10 software.

Western-Blot Analysis

Tissue samples were collected from the lungs of treated mice. These samples were snap-frozen in liquid nitrogen and kept at −80° C. until ready to be used. Tissue lysates were prepared in Pierce® RIPA buffer (Thermo Scientific, Rockford, Ill.) with addition of PIERCE™ Protease Inhibitor Mini Tablets (Thermo Scientific, Rockford, Ill.). Protein concentration was determined with the COOMASSIE PLUS™ (Bradford) Assay Kit (Thermo Scientific, Rockford, Ill.). 80 µg of total proteins was separated on NuPAGE 4-12% Bis-Tris gels (Life Technologies, Carlsbad, Calif.) with NuPAGE MES SDS running buffer (Life Technologies, Carlsbad, Calif.) and subsequently transferred onto nitrocellulose membrane of 0.45 µm pore size (Life Technologies, Carlsbad, Calif.). Blocking was carried out according to manufacturer's instructions (Invitrogen, Carlsbad, Calif.) for 1 hour at room temperature and probed with Rabbit antihuman DNMT3B monoclonal antibody (1:500) and Mouse antihuman β-tubulin antibody (1:5000) overnight at 4° C. The membranes were washed 5 min, thrice in wash buffer (Invitrogen, Carlsbad, Calif.).

Membranes were then incubated with secondary goat anti-mouse antibodies, conjugated with horseradish peroxidase (Molecular Probes, Eugene, Oreg.) at a dilution 1:1000. Immune complexes were detected Pierce ECL Western Blotting Substrate (Thermo Scientific, Rockford, Ill.) in a dark room on table top processor SRX-101A (Konica Minolta, Japan). Images were quantified in the Image J software.

Western Blot Analysis

One million A549 cells per well were seeded in culture dish and incubated for 48 hours. Cells were treated with MUC1 aptamer-functionalized miR-29b-loaded hybrid nanoparticles (at an equivalent concentration of 100 nM of miRNA-29b), MUC1 aptamer-functionalized negative control miRNA-loaded hybrid nanoparticles as well as miR-29b in Lipofectamine 2000 reagent in Opti-MEM medium for 3 days. Cells were lysed in Pierce® RIPA buffer (Thermo Fisher Scientific) with addition of Pierce™ Protease Inhibitor Mini Tablets (Thermo Fisher Scientific) for 30 minutes on ice and centrifuged for 10 minutes at 10,000×g at +4° C. The protein concentration was determined with the Coomassie Plus™ (Bradford) Assay Kit (Thermo Fisher Scientific). A total of 120 μg of total proteins was separated on NuPAGE 4%-12% Bis-Tris gels (Thermo Fisher Scientific) with NuPAGE MES SDS running buffer (Thermo Fisher Scientific) and subsequently transferred onto a nitrocellulose membrane with a pore size of 0.22 μm (Thermo Fisher Scientific). The membrane with proteins was blocked according to manufacturer's instructions (Thermo Fisher Scientific) for 1 hour at room temperature and probed with primary antibodies overnight at 4° C. DNMT3B (1:1,000, Thermo Fisher Scientific) and MCL1 (1:500; Thermo Fisher Scientific). β-Tubulin was used as a housekeeping gene (1:2,000, Sigma-Aldrich). Next day the membranes were washed three times for 5 minutes in wash buffer according to manufacturer's instructions (Thermo Fisher Scientific) and incubated with secondary goat antimouse (Molecular Probes, Eugene, Oreg.) or goat antirabbit (1:1,000, Thermo Fisher Scientific) secondary antibodies, conjugated with horseradish peroxidase at a dilution of 1:1,000.

Immune complexes were detected with chemiluminescent substrate, Pierce ECL Western Blotting substrate (Thermo Fisher Scientific), in a dark room on tabletop processor SRX-101A (Konica Minolta, Tokyo, Japan).

Cell Viability

MTT assay was used to determine the effect of MUC1 aptamer-functionalized miRNA-29b-loaded hybrid nanoparticles on the proliferation of A549 cells. Cells ($1\times10^4$) per well were seeded in 96-well plates and incubated at 37° C. in a humidified atmosphere with 5% carbon dioxide for 24 hours. The cells were then treated with different concentrations of miRNA-29b-loaded hybrid nanoparticles in Opti-MEM for 7 hours before being replaced with F12 K medium supplemented with 10% FBS and 1% antibiotics. This was then incubated for 72 hours. miRNA-29b transfected with NeoFX transfection agent was used as control in this experiment. Approximately 10 μL of 12 mmol/L MTT reagent was then added to each well. This was then incubated at 37° C. for 4 hours. The medium was aspirated, and 50 μL of sterile dimethyl sulfoxide were added to each well and mixed thoroughly with pipette. The cells were then incubated at 37° C. for 10 minutes. The plate was read at 540 nm and 650 nm.

Animals

Female severe combined immunodeficient (SCID) beige mice, 8 weeks old were obtained from Taconic Co. (Hudson, N.Y.). These mice weighed approximately 25 g.

Animal Treatment and Blood Sampling for Pharmacokinetic and Biodistribution Studies Female SCID beige mice were injected with $5\times10^5$ A549-luciferase cells suspended in sterile PBS to create metastatic models of NSCLC. Xenogen IVIS bioluminescence imaging system was used to monitor tumor growth by administering 100 μl of 30 mg/ml Xenolight Rediject D-Luciferein intraperitoneally into the mice approximately ten minutes before imaging. Once tumors were established, tumor-bearing mice were divided into three groups of three animals each. The first group was treated with MAFMILHN containing an equivalent miRNA-29b dose of 1.5 mg/kg twice weekly. The second group was treated with MUC1-aptamer functionalized control miRNA-loaded hybrid nanoparticles (NC-nano) containing an equivalent control miRNA dose of 1.5 mg/kg twice weekly by intraperitoneal injection. The third group was treated with PBS twice weekly also, by peritoneal injection. Nanoparticles were dispersed in sterile PBS. All mice were treated for a total of four weeks.

Tumor burden was monitored using Xenogen IVIS bioluminescence imaging system. For biodistribution and pharmacokinetic study, tumor bearing SCID beige mice were divided into two groups of three animals each. The first group was treated with a single dose of MAFMILHN loaded with an equivalent dose of 1.5 mg/kg miRNA-29b. The second group was treated with a single dose of non-functionalized miRNA-29b loaded hybrid nanoparticles loaded with an equivalent dose of 1.5 mg/kg. Blood samples were collected from each group per time point at 0, 30 and 60 min, and 24, 26 and 48 h post-dose by retro-orbital puncture into EDTA tubes.

Animals were also sacrificed 48 h posttreatment to harvest the lungs, kidneys, heart and livers for analysis. Blood samples were mixed with equal amount of Lysis-loading buffer of Clarity OTX kit (Phenomenex, CA) and stored at −80° C. until ready to be used. Tissues were snap-frozen in the liquid nitrogen stored at −80° C. before analysis.

Pharmacokinetic (PK) Data Analysis

WinNonlin software version 6.0 (Pharsight, Mountain View, Calif.) was used for the estimation of PK parameters using non-compartment analysis of the composite data.

Hyperspectral Microscopy

Cells and lung tissue section slides were prepared for hyperspectral microscopy. Hyperspectral images were captured at 60× magnification under enhanced darkfield illumination using the CytoViva hyperspectral imaging system (Auburn, Ala.). This hyperspectral imaging system couples an enhanced darkfield illuminator with a CCD attached to a visible near-infrared (VNIR) diffraction grating spectrograph. The hyperspectral images, also called data cubes, were collected using the "push broom" method facilitated by an automated motorized stage. The spectral data (400-1000 nm) was acquired one pixel row at a time. A version of ENVI imaging and analysis software proprietary to CytoViva was used to compile the spectral and spatial data into a data cube, in which each pixel contained spectral data. Spectral libraries corresponding to the nanoparticles and tissue were built from the hyperspectral images of the functionalized and non-functionalized nanoparticles as well as the exposed tissue. These libraries were filtered against a negative control image (tissue only) to ensure no false-positive mapping of the nanoparticles. Using the Spectral Angle Mapper (SAM) algorithm, the spectral libraries were compared to their respective images. The pixels in the exposed sample whose spectra matched a spectrum in the library for the functionalized nanoparticles were pseudo-colored red, confirming the presence of the nanoparticles.

Statistical Analysis

Results are presented as mean±SD, unless otherwise indicated. Statistically significant difference between two groups was determined by two-tailed Student's t-test. A P-value of 0.05 was taken as statistically significant.

Example 1: Nanoparticle Characterization

Particle size and zeta potential analysis by photon correlation spectroscopy, shown in Table 1, demonstrated that non-functionalized hybrid nanoparticles were about 240 nm in size, while MUC1 aptamer-functionalized hybrid nanoparticles were about 595 nm in size. Non-functionalized hybrid nanoparticles were negatively charged with a zeta potential of −2.1, while the conjugation of MUC1 aptamer increased the zeta potential of these nanoparticles to +4.1.

TABLE 1

Particle size and zeta potential of non-functionalized and aptamer-functionalized hybrid nanoparticles (mean ± SD, n = 3)

| Nanoparticle sample | Mean diameter (nm) | Polydispersity index | Zeta potential (mV) |
|---|---|---|---|
| Non-functionalized nanoparticles | 236.2 ± 35.1 | 0.242 ± 0.007 | −2.1 ± 1.7 |
| Aptamer-functionalized nanoparticles | 595.9 ± 43.1 | 0.554 ± 0.386 | +4.1 ± 1.0 |

Figure 1B:
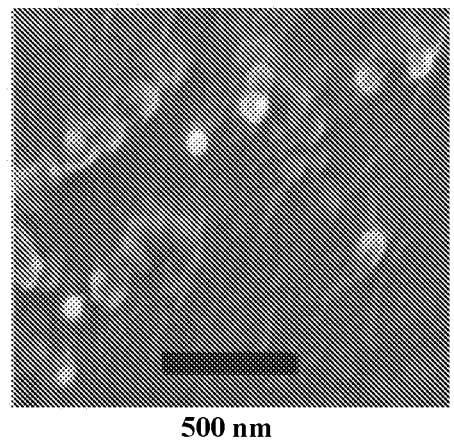
Figure 1C:
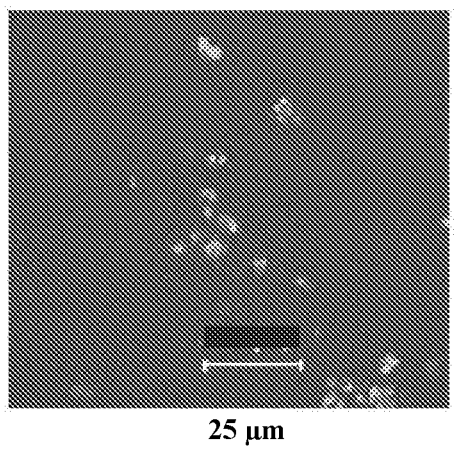

The schematic of the MUC1 aptamer-functionalized hybrid nanoparticle is shown in FIG. 1A. Scanning electron micrograph in FIG. 1B reveals that the hybrid nanoparticles were spherical in shape with smooth surface.

miRNA encapsulation efficiency (EE) and loading capacity (LC) were measured using ion-pair HPLC analysis of the filtrates obtained by centrifuging the nanoparticles formed to determine the amount of unencapsulated miRNA-29b. EE and LC were calculated using the following equation:

$$\% \ EE = (A-B) \times 100/A, \text{ and } \% \ LC = (A-B) \times 100/C \quad (1)$$

where A=total amount of miRNA, B=free miRNA, and C=weight of hybrid nanoparticles in grams.

EE was calculated to be 98.8%±0.4%, whereas LC was calculated to be 8.6%±0.1%.

Figure 1D:
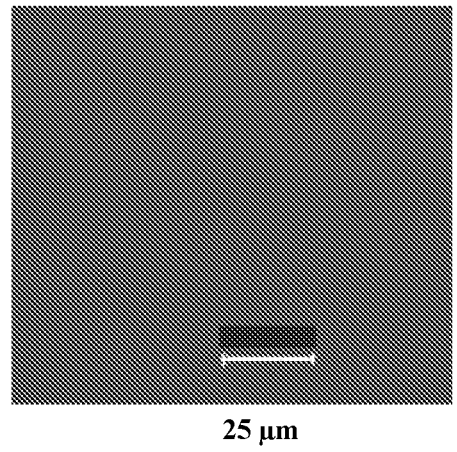
Figure 1E:
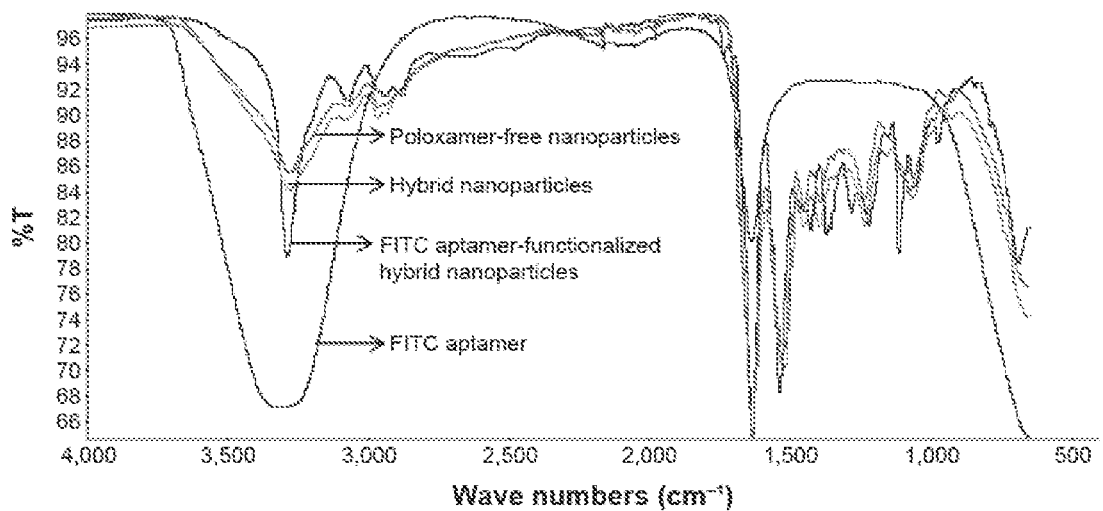

Conjugation of MUC1 aptamer to the surface of the nanoparticles was verified using fluorescence microscopy. FIG. 1C demonstrates the successful conjugation of FITC-MUC1 aptamer to the nanoparticles by the presence of fluorescent green color in the micrograph. In contrast, non-functionalized hybrid nanoparticles in FIG. 1D showed the absence of fluorescent green color, confirming the lack of FITC-MUC1 aptamer in the nanoparticles. Fourier transform-infrared (FT-IR) was also used to confirm the successful conjugation of MUC1 aptamer to the nanoparticles. FIG. 1E shows the FT-IR spectra generated from functionalized and non-functionalized hybrid nanoparticles. A distinctive and conspicuous difference between these sets of spectra bears testament to the successful conjugation of MUC1 aptamer to the hybrid nanoparticles.

Example 2: In Vitro Release Study

The release of miRNA-29b from MUC1 aptamer-functionalized hybrid nanoparticles was compared at pH values 5, 6.6, and 7.4. FIG. 2 demonstrates a limitation in the release of miRNA-29b at pH values 6.6 and 7.4 when compared with the release profile at pH 5.

Example 3: Expression of MUC1 Protein in NSCLC Cells

Reverse transcriptase PCR was used to confirm the expression of MUC1 in two NSCLC cells, A549 and H460, to ensure that these cells actually express MUC1. FIG. 3A demonstrates the relatively higher expression of MUC1 in both cancer cells when compared with normal lung fibroblast cell line MRC-5.

Example 4: Cellular Uptake of MUC1 Aptamer-Functionalized Hybrid Nanoparticles

Internalization of nanoparticles was evaluated using both flow cytometry and fluorescence microscopy. Flow cytometry was used to compare nanoparticle uptake by A549 and MRC-5. siGLO-FAM (green) was used as a model small double-stranded RNA labeled with FAM (a green dye). MUC1 aptamer conjugated to siGLO-loaded hybrid nanoparticles used in this experiment was bereft of FITC so as to avoid double fluorescence. As shown in FIG. 3B, internalization of MUC1 aptamer-functionalized siGLO-FAM-loaded nanoparticles in A549 cells was significantly higher (P≤0.001) in non-inhibited cells when compared with cells pretreated with MUC1 aptamer. Furthermore, uptake of nanoparticles by MRC-5 was much lower than the uptake by A549 cells.

Fluorescence microscopy was used to study the interaction of FITC-MUC1 aptamer-functionalized hybrid nanoparticles with the cell membrane of A549 cells. FIG. 4A demonstrates the presence of FITC-MUC1 aptamer-functionalized hybrid nanoparticles (green color) on the cell membrane and inside the cytosol of A549 cells after 2 hours of incubation. Cell membrane of cells was stained with WGA-Alexa Fluor 555 (red color) to enable the identification of the boundaries of cells. Without wishing to be limited by any theory, colocalization of both green and red colors on the membrane of the cells suggests a possible interaction between the FITC-MUC1 aptamer-functionalized hybrid nanoparticles and the membrane of the cells possibly due to the presence of MUC1 on the membrane.

Intracellular trafficking of internalized nanoparticles was also monitored using fluorescence microscopy. Late endosomes/lysosomes were labeled with LysoTracker-Red to enable the monitoring of the fate of internalized nanoparticles. FIG. 4B demonstrates maximum level of colocalization of siGLO-FAM and LysoTracker-Red after 2 hours of incubation. However, after 4 hours, the siGLO-FAM was observed to be leaving the late endosomes and moving into the cytoplasm as indicated by the numerous green colored dots surrounding the nucleus.

Figure 7A:
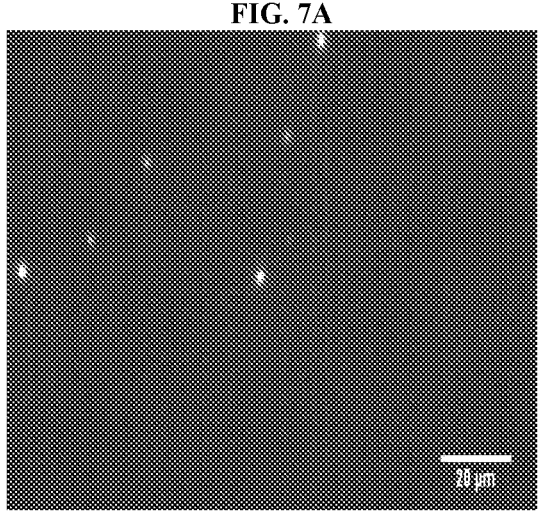
FIGS. 7A-7H illustrate hyperspectral imaging of nanoparticle internalization.
Figure 7B:
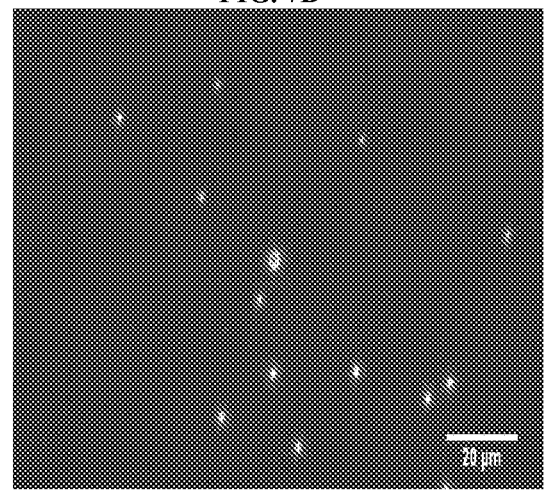
Figure 7C:
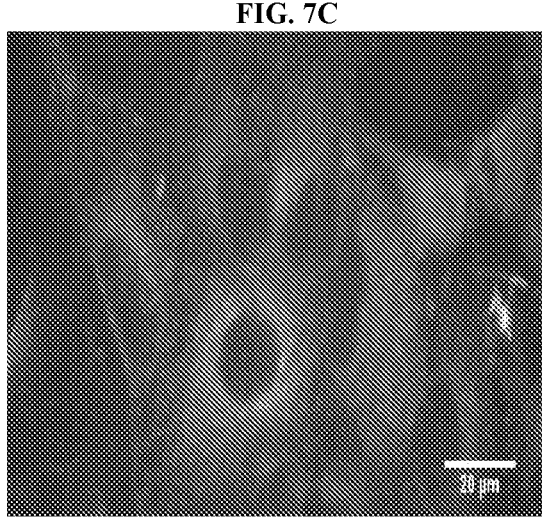
Figure 7D:
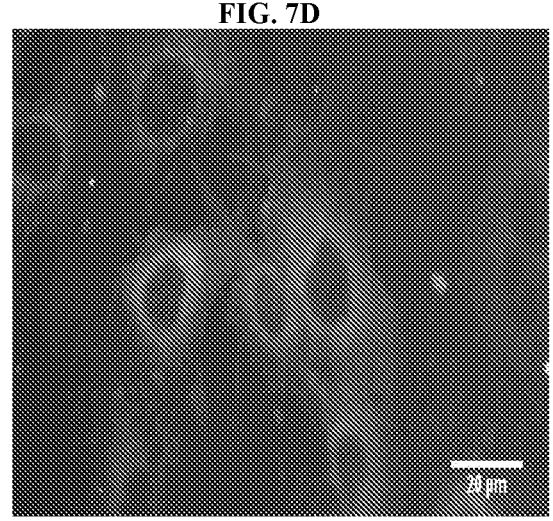
Figure 7E:
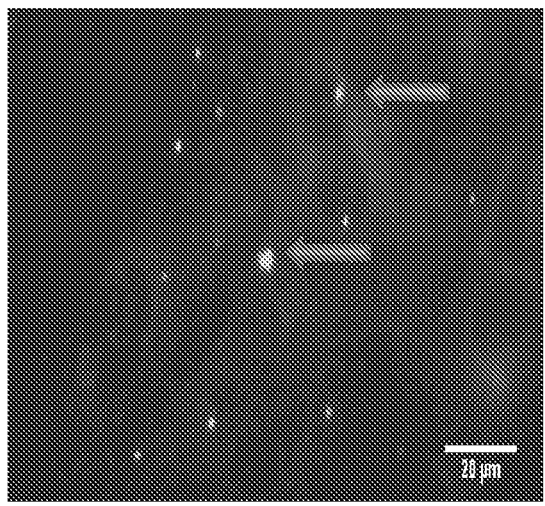
Figure 7F:
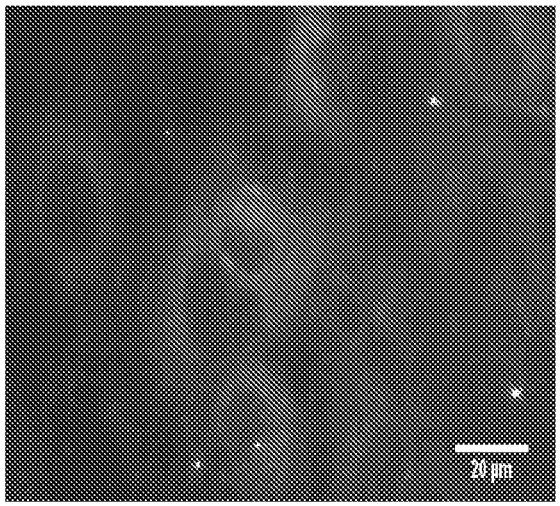
Figure 7G:
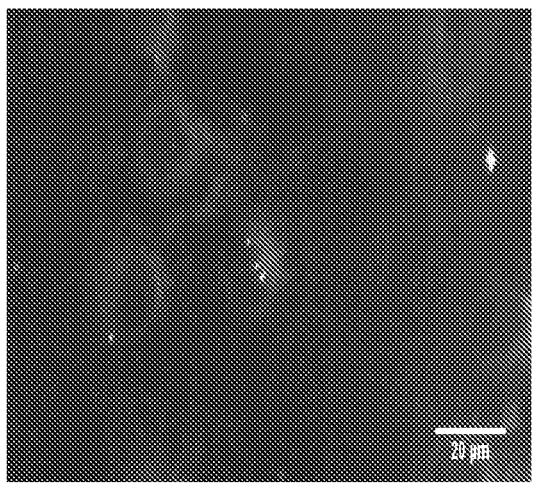
Figure 7H:

Cellular uptake was further monitored with hyperspectral microscopy (Cytoviva Inc. Auburn, AL). FIGS. 7A-7H show micrographs captured by hyperspectral microscopy. FIGS. 7A-7B demonstrate the spherical morphology of both MAFMILHN and non-functionalized miRNA-29b-loaded hybrid nanoparticles. This is consistent with the image of the morphology obtained by SEM in FIG. 6. FIGS. 7C-7D show the untreated A549 and MRC5 cells respectively, showing lack of presence of nanoparticles in the cells. However, FIG. 7E demonstrates the presence of numerous MAFMILHN in A549 cells following 2h-treatment. This is in contrast to A549 cells in FIG. 7F treated with non-functionalized hybrid nanoparticles, showing limited amount of internalized nanoparticles. This demonstrates the influence of MUC1-aptamer in the uptake of these nanoparticles. FIGS. 7G-7H demonstrate that both MAFMILHN and non-functionalized hybrid nanoparticles were not taken up significantly by MRCS due to the limited expression of MUC1 in this cell.

Example 5. Tissue Distribution and Pharmacokinetic Study

Figure 8A:
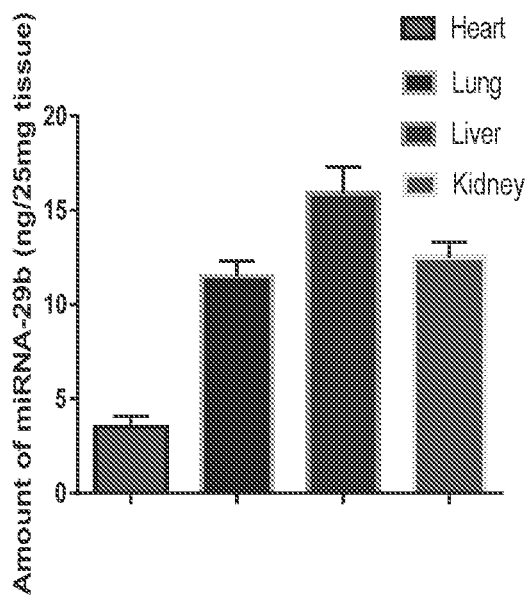
Figure 8B:
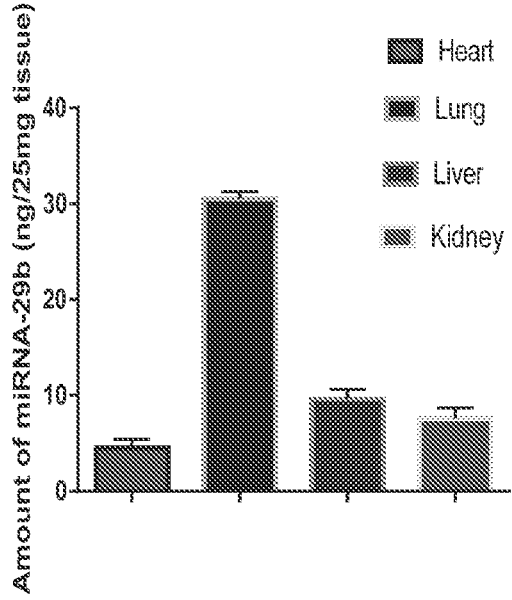

Following the harvest of essential organs from euthanized lung-tumor bearing SCID beige mice, the deposition of miRNA-29b in the heart, tumor-bearing lungs, kidney and liver was quantified. FIGS. 8A-8B demonstrate the importance of MUC1-aptamer in ensuring that miRNA-29b loaded in MAFMILHN was preferentially delivered to tumor bearing lungs while limiting accumulation in healthy organs such as kidney, liver and heart. In the absence of MUC1-aptamer, as demonstrated in FIG. 8B, non-selective delivery of miRNA-29b was observed by non-functionalized hybrid nanoparticles with more miRNA-29b detected in the liver and kidney than in the lungs. This demonstrates the importance of MUC1-aptamer in targeted delivery of miRNA-29b to lung tumor with minimal delivery to other organs. To visualize the presence of nanoparticles in the lungs, tissue sections of lungs obtained from the two experimental groups were imaged using hyperspectral microscopy. FIG. 8C shows high deposition of MAFMILHN in lung tumor of mice treated with these nanoparticles. In contrast, lung tumor of mice treated with non-functionalized miRNA-29b loaded hybrid nanoparticles show limited amount of nanoparticles (FIG. 8D), further demonstrating the selective and specific delivery of miRNA-29b using MUC1-aptamer functionalized hybrid nanoparticles.

FIG. 9 demonstrates the plasma concentration versus time curves when equivalent of 1.5 mg/kg of miRNA-29b in MAFMILHN. The maximum concentration ($C_{max}$) of miRNA-29b delivered MAFMILHN was 15289.5 ng/ml, slightly lesser than 18289.5 ng/ml observed for the non-functionalized miRNA-29b-loaded hybrid nanoparticles. These maximum concentrations were observed at 60 mins ($T_{max}$) for both nanoparticles.

Key pharmacokinetic parameters presented in Table 2 further demonstrate the similarities in the pharmacokinetics of both MAFMILHN and non-functionalized miRNA-29b-loaded hybrid nanoparticles. Both MAFMILHN and non-functionalized miRNA-29b-loaded hybrid nanoparticles produced a half-life of 13.3 and 14.6 h respectively. Further, both formulations produced similar men residence time (MRT) and apparent clearance.

TABLE 2

Key pharmacokinetic parameters of miRNA-29b loaded in MAFMILHN and non-functionalized hybrid nanoparticles in orthotopic SCID models of NSCLC.

| Parameters | MAFMILHN | Non-functionalized hybrid nanoparticles |
|---|---|---|
| $C_{max}$ ng/ml | 15289.5 | 18289.5 |
| $T_{max}$ (h) | 1.0 | 1.0 |
| $AUC_{last}$ (h · ng/ml) | 443991.8 | 540341.8 |
| CL/F (ml/min/kg) | $5.04 \times 10^{-8}$ | $4.04 \times 10^{-8}$ |
| $\lambda_z$ (1/h) | 0.05208 | 0.04763 |
| $T_{1/2}$ (h) | 13.3 | 14.6 |
| MRT (h) | 16.4 | 16.7 |
| $V_Z/F$ (1/kg) | $5.8 \times 10^{-5}$ | $5.1 \times 10^{-5}$ |

$C_{max}$ = Peak plasma concentration;
$T_{max}$ = Time to peak plasma concentration;
$AUC_{last}$ = area under the plasma concentration-time curve from time zero to time of last measurable concentration;
CL/F = Apparent clearance;
$\lambda_z$ = Elimination rate constant;
$T_{1/2}$ = Plasma terminal half-life;
MRT = Mean residence time;
$V_Z/F$ = Apparent volume of distribution.

Example 6: MUC1 Aptamer-Functionalized miRNA-29b-Loaded Hybrid Nanoparticles Downregulate DNMT3B and MCL1 Proteins and Induce Apoptosis in A549 Cells FIG. 5A demonstrates the knockdown efficiency of MUC1 aptamer-functionalized miRNA-29b-loaded nanoparticles against DNMT3B. These nanoparticles produced superior downregulation of DNMT3B when compared with Lipofectamine 2000 transfected miRNA-29b and the negative control miRNA-loaded nanoparticles. FIG. 5B further demonstrates the superior transfection efficiency of MUC1 aptamer-functionalized miRNA-29b-loaded nanoparticles in comparison to lipofectamine by effectively downregulating MCL1. In contrast, both lipofectamine and MUC1 aptamer-functionalized negative control miRNA-loaded hybrid nanoparticles did not achieve the same level of downregulation.

Figure 5C:
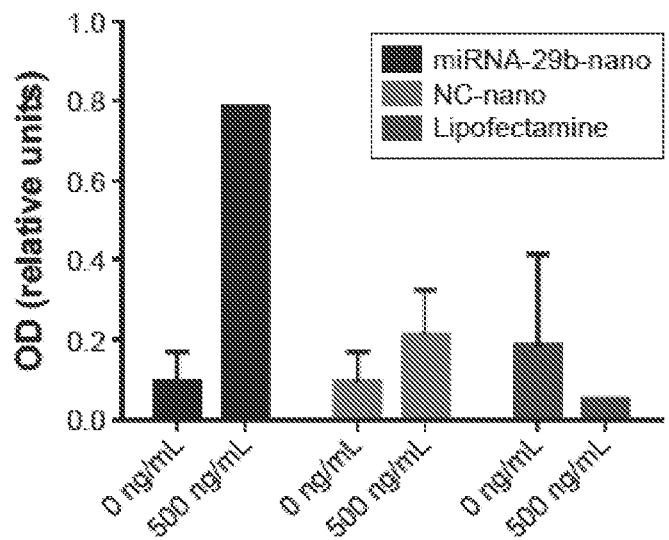

Superior induction of apoptosis was observed in A549 cells treated with MUC1 aptamer-functionalized miRNA-29b-loaded hybrid nanoparticles when compared with non-treated cells, MUC1 aptamer-functionalized negative control miRNA-loaded hybrid nanoparticles-treated cells and lipofectamine-transfected miRNA-29b (FIG. 5C).

Figure 5D:
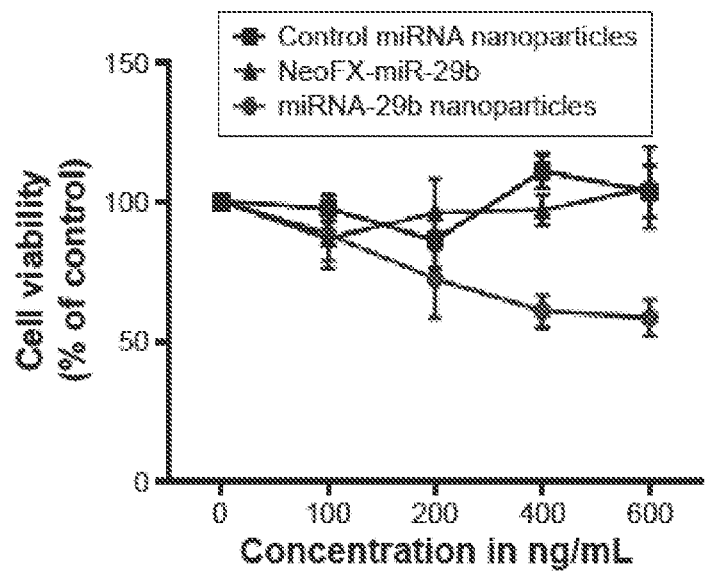

Antiproliferative effect of MUC1 aptamer-functionalized miRNA-29b-loaded nanoparticles was evaluated using MTT assay and compared with that of NeoFX-transfected miRNA-29b and negative control miRNA-loaded nanoparticles in A549 cells. As demonstrated in FIG. 5D, MUC1 aptamer-functionalized miRNA-29b-loaded nanoparticles were significantly more cytotoxic to A549 cells than NeoFX-transfected miRNA-29b and negative control miRNA-loaded miRNA nanoparticles.

Figure 10A:
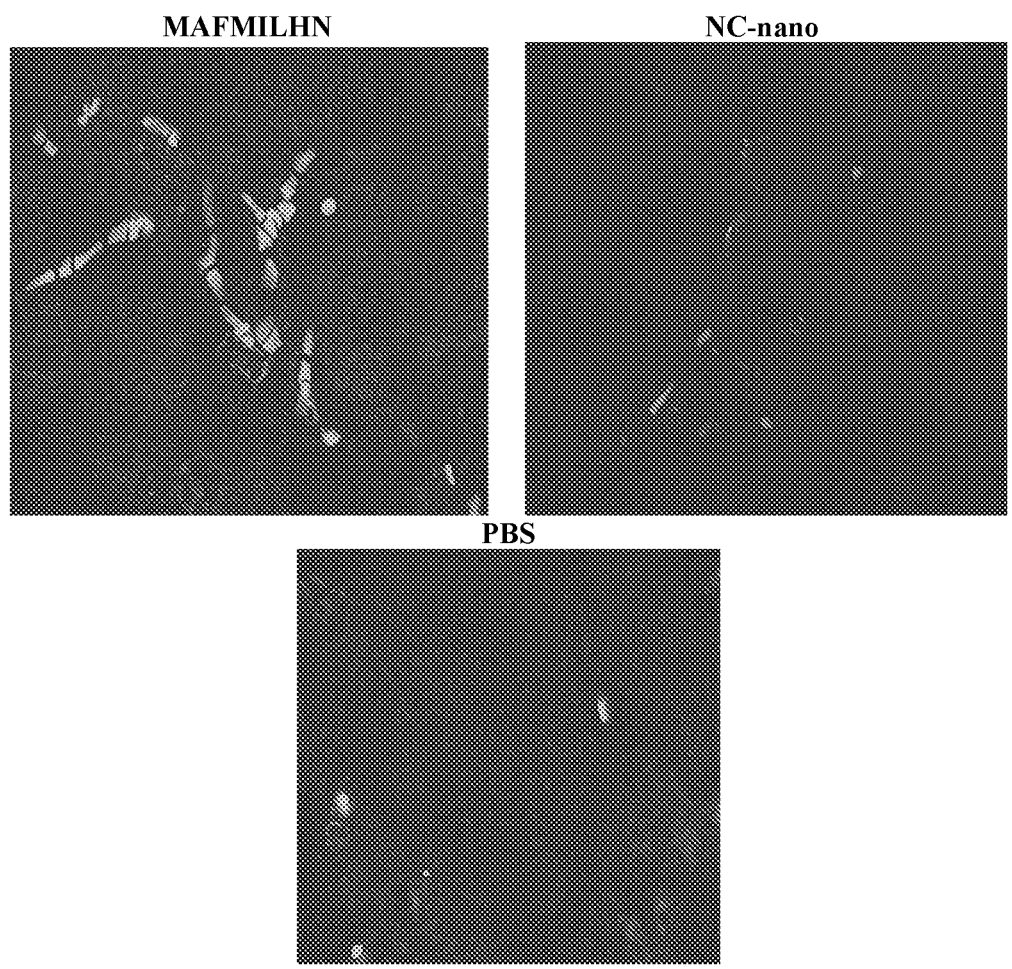
FIGS. 10A-10B illustrate apoptosis in treated tumor-bearing lungs.
Figure 10B:
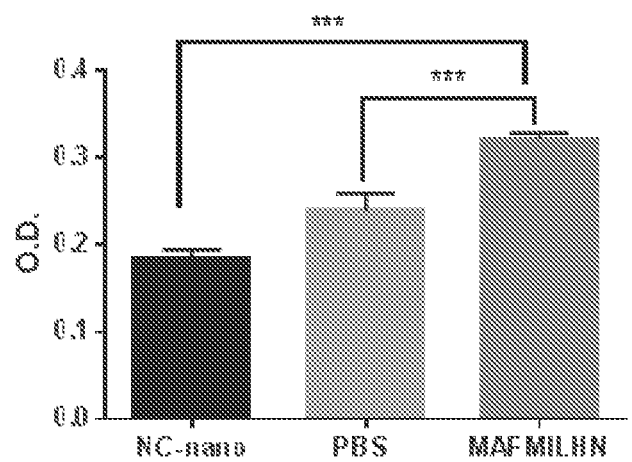

The ability of MAFMILHN to induce apoptosis in lung tumor was evaluated using both TUNEL assay and cell death-detection ELISA. The lungs of tumor-bearing mice treated with MAFMILHN demonstrated high level of apoptosis as measured by TUNEL in FIG. 10A. Conversely, mice treated with NC-nano and PBS demonstrated very low level of apoptosis. Results generated form TUNEL assay was validated with cell death-ELISA data presented in FIG. 10B. Similar to the TUNEL results, cell death ELISA showed that apoptosis in the lungs of mice treated with MAFMILHN was significantly higher than in the lungs of mice treated with NC-nano and PBS.

Figure 11A:
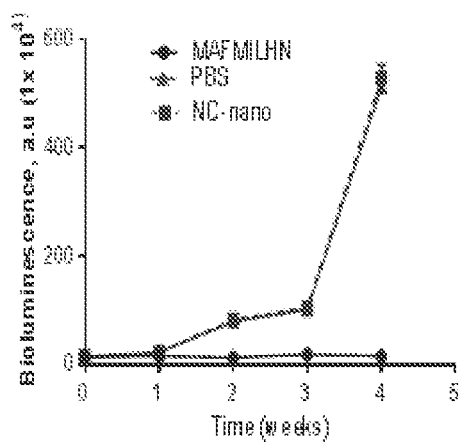
FIGS. 11A-11B illustrate in vivo antitumor effect in SCID beige mice monitored using IVIS bioluminescence imaging system.
Figure 11B:
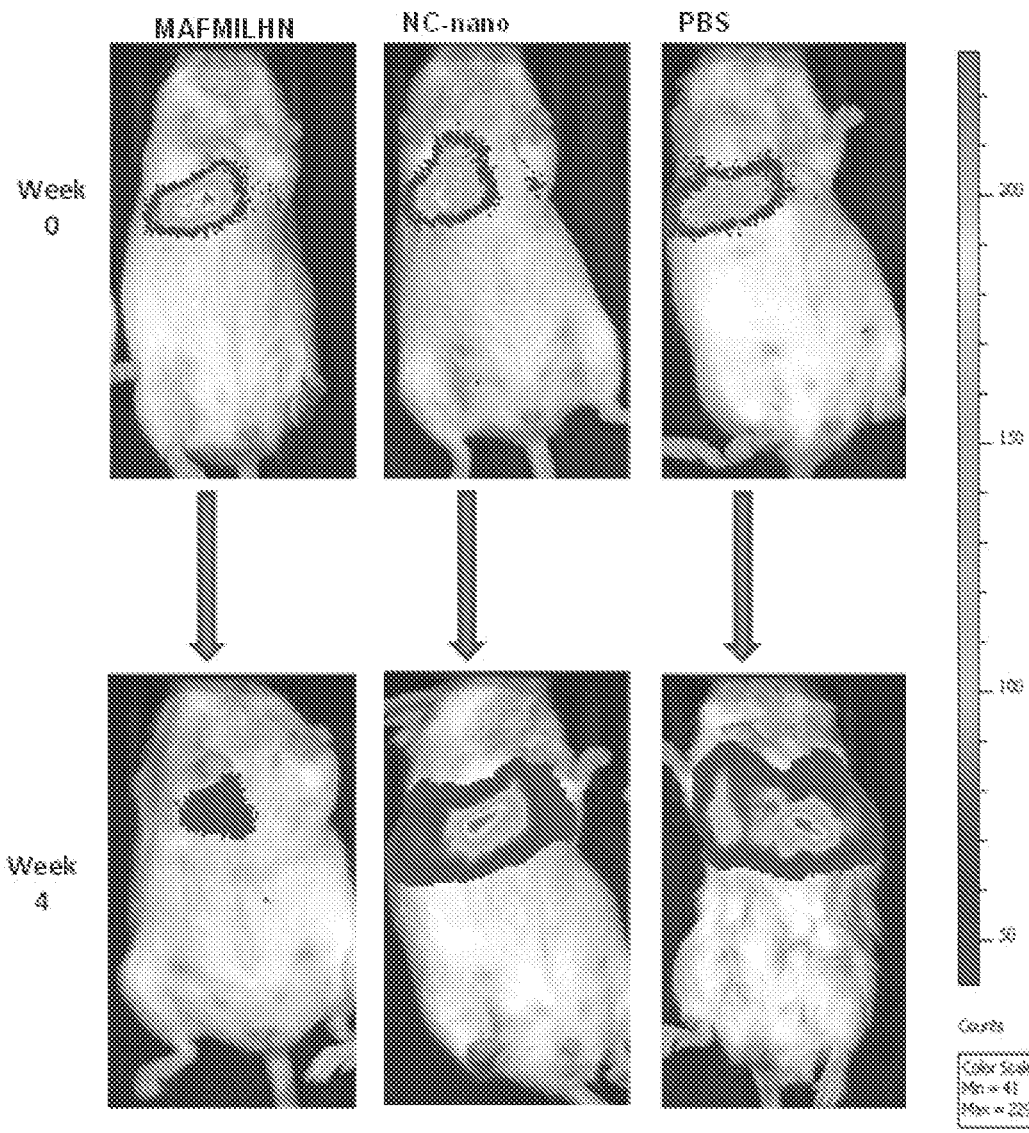

Tumor suppression capability of MAFMILHN was evaluated using IVIS bioluminescence imaging system to monitor tumor burden in tumor-bearing SCID mice over a four-week period. FIGS. 11A-11B demonstrate the ability of MAFMILHN to suppress tumor growth when compared to different controls. In FIG. 11A, the intensity of bioluminescence was quantified and plotted against time. While the tumor in mice treated with NC-nano and PBS continued to grow over the study period, tumor in mice treated with MAFMILHN decreased in intensity over the same period. Representative bioluminescence images are shown in FIG. 11B. These images are constituent with the graphical presentation in FIG. 11A.

Example 7

As demonstrated herein, the ability of MUC1-aptamer functionalized miRNA-29b-loaded hybrid nanoparticles (MAFMILHN) to selectively deliver miRNA-29b to lung tumor while limiting accumulation in healthy tissues was demonstrated. The described pharmacokinetic (PK) studies helped determine some critical PK parameters for MAFMILHN.

MAFMILHN nanoparticles were prepared, and conjugation of MUC1-aptamer to the hybrid nanoparticles increased the particle size from 236 nm to 595 nm. Without wishing to be limited by any theory, the change in size can be at least partially explained by the presence of the aptamer on the surface of the nanoparticles, along with the extra steps involved in the conjugated process, especially the use of lyophilization, which could lead to agglomeration of particles. This is further reflected in the polydispersity index (PDI) increase from 0.243 to 0.554 following the aptamer conjugation procedure.

Intracellular delivery of the nanoparticles in both A549 cells and lung tumor tissues were probed using hyperspectral microscopy. Hyperspectral microscopy, which was developed to address current analytical challenges for nanoscale materials, combines hyperspectral imaging (HSI) with advanced optics, typically focusing on specialized dark-field reflectance systems. Hyperspectral microscopy data in FIGS. 7A-7H confirms the selective delivery of MAFMILHN to mucin expressing cells in comparison to cell with limited mucin-1 expression. A549 cells showed very high level of expression of mucin-1 as compared to MRC-5, which showed very limited level of mucin-1. Hyperspectral microscopy showed that MAFMILHN were preferentially delivered to A549 cells when compared to MRC-5. This correlates with the comparative level of mucin-1 in both cells. Further, hybrid nanoparticles that were not conjugated with MUC1-aptamer were not efficiently delivered to either A549 cells or MRC-5.

The effect of MUC1-aptamer on the selective delivery of MAFMILHN to tumor tissues in mouse models and compared to non-functionalized hybrid nanoparticles. MAFMILHN were found to favorably deliver miRNA-29b to tumor-bearing lung tissues in contrast to heart liver and kidney in FIG. 8A. However, the non-functionalized hybrid nanoparticles were not able to achieve this in FIG. 8B. Further, hyperspectral microscopy images in FIGS. 8C-8D were able to confirm that MAFMILHN were indeed accumulated in tumor bearing lung tissue, while such could not be said for non-functionalized hybrid nanoparticles. The liver and kidneys also had minor amounts of miRNA-29b delivered to them by MAFMILHN. The liver amongst other organs such as spleen belongs to the reticuloendothelial endothelial system organs. In certain non-limiting embodiments, the liver, being a highly perfused organ, enables rapid distribution of nanoparticles to this organ, whether the nanoparticle is targeted or not. In addition, the microvessels of liver have relatively large fenestrations, which allow entry of particles as high as approximately 200 nm. The kidney also demonstrated a limited amount of miRNA-29b from MAFMILHN; in certain non-limiting embodiments, this organ is highly perfused and the main organ for elimination. Although limited amount of miRNA-29b was delivered to tumor-bearing lungs by non-functionalized hybrid nanoparticles regardless of these nanoparticles not being functionalized by MUC1-aptamer.

The pharmacokinetic parameters of both MAFMILHN and that of the non-functionalized hybrid nanoparticles were very similar, suggesting that, although the conjugation of MUC1-aptamer to the nanoparticles in MAFMILHN enhanced the discriminatory delivery of miRNA-29b to lung tumor tissues, it did not influence the peak plasma concentration ($C_{max}$), time to peak plasma concentration ($T_{max}$), area under the plasma concentration-time curve from time zero to time of last measurable concentration ($AUC_{last}$), apparent clearance (CL/F), elimination rate constant ($\lambda_z$), plasma terminal half-life ($T_{1/2}$), mean residence time (MRT) and apparent volume of distribution to any significant extent when compared to the non-functionalized hybrid nanoparticles. In certain non-limiting embodiments, the presence of the nanoparticles in both formulations protect the loaded miRNA-29b from marauding endonuclease enzymes and phagocytes, hence helping to enhance the circulation time of miRNA-29b in the blood.

To evaluate the ability of MAFMILHN to downregulate target oncoprotein DNMT3B in both in vitro and in vivo models, its expression was monitored using western blot. As demonstrated in FIG. 5A, DNMT3B was downregulated in A549 cells following treatment with MAFMILHN in a superior version when compared to lipofectamine-transfected miRNA-29b as well as MUC1-aptamer functionalized control miRNA-29b-loaded hybrid nanoparticles. This result was consisted in SCID mice (in vivo), as demonstrated by the result in FIG. 5B in which MAFMILHN was able to complete downregulate the expression of DMNT3B. DNMT3B is a member of the DNA methyltrasferase family that accounts for the inactivation of tumor-suppressor genes in many cancer cells. However, miRNA-29b is known to exert its tumor-suppressive role by directly targeting DNMT3B in cancer cells. Without wishing to be limited by any theory, downregulation of DNMT3B can lead to the induction of apoptosis in tumor tissues, hence leading to the inhibition of tumor growth in SCID mouse models. FIGS. 10A-10B and 11A-11B indicate that apoptosis was observed in treated mice, which consequently led to the inhibition of tumor growth in the animals.

Taken together, the present results indicate that MUC1-aptamer functionalized hybrid nanoparticles can be used as a platform targeted nanoparticle delivery system for efficient delivery of miRNAs, especially miRNA-29b to non-small cell lung cancer for the downregulation of target oncogene.

The disclosures of each and every patent, patent application, and publication cited herein are hereby incorporated herein by reference in their entirety. One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the present invention. The appended claims are intended to be construed to include all such embodiments and equivalent variations.

What is claimed:

1. A protein-containing nanoparticle,
wherein the core of the nanoparticle comprises at least one protein selected from the group consisting of
a plasma protein selected from the group consisting of an albumin, a fibrinogen, and a globulin,
an IgG,
a cytokine selected from the group consisting of an interleukin, erythropoietin, an interferon, and filgrastim,
an immunomodulator comprising cyclosporine,
a hormone selected from the group consisting of insulin, glucagon and somatotropin, and
an enzyme selected from the group consisting of a blood clotting factor, adenosine deaminase and an alpha antitrypsin,
wherein the at least one protein is in a neutral state in the nanoparticle,
wherein the nanoparticle is surrounded by a layer comprising a stealth polymer,
wherein the nanoparticle further comprises at least one aptamer such that
at least one protein beneath the stealth polymer layer is covalently conjugated with the at least one aptamer,
the at least one aptamer spans the stealth polymer layer, and at least a fraction of the at least one aptamer is displayed on the outer surface of the protein-containing nanoparticle.

2. The nanoparticle of claim 1, wherein the stealth polymer is at least one selected from the group consisting of an alkyl polyethylene glycol, an alkylphenol oxide, a copolymer of polyethylene glycol and polypropylene oxide, a polyethylene glycol, a polypropylene glycol, a polyvinylpyrrolidone (PVP), a polyvinyl alcohol, or any combinations thereof.

3. The nanoparticle of claim 1, which has a diameter ranging from about 10 nm to about 1,000 nm.

4. A composition comprising at least one protein nanoparticle of claim 1, which is prepared by a method comprising:
adjusting the pH of a first solution comprising the protein to about the isoelectric point of the protein, thereby forming a first protein nanoparticle, which comprises at least a fraction of the protein;
wherein at least one protein in the first protein nanoparticle is further conjugated with the at least one aptamer;
and,
contacting the first protein nanoparticle with a second solution comprising the stealth polymer, wherein the concentration of the stealth polymer in the second solution ranges from about 0.1% to about 20,000% of the CMC of the stealth polymer, thereby forming at least one protein nanoparticle.

5. The composition of claim 4, wherein the first solution further comprises at least one therapeutic agent, and wherein the first protein nanoparticle comprises at least a fraction of the at least one therapeutic agent.

6. The composition of claim 5, wherein the at least therapeutic agent is selected from the group consisting of an organic compound, inorganic compound, pharmacological drug, antibody, radiopharmaceutical, protein, peptide, polysaccharide, nucleic acid, siRNA, miRNA, RNAi, short hairpin RNA, antisense nucleic acid, ribozyme and dominant negative mutant.

7. The composition of claim 6, wherein the antibody comprises a monoclonal antibody selected from the group consisting of bevacizumab, anatumomab, benralizumab, enokizumab, mitumomab, oxelumab, and palivizumab.

8. The composition of claim 4, wherein the at least one aptamer binds to at least one selected from the group consisting of neurotensin receptor-1, human epidermal growth factor receptor-2 (HER-2), folate receptor, insulin-like growth factor receptor (IGF), and epidermal growth factor receptor (EGFR).

9. The composition of claim 4, wherein the stealth polymer comprises at least one selected from the group consisting of an alkyl polyethylene glycol, an alkylphenol oxide, a copolymer of polyethylene glycol and polypropylene oxide, a polyethylene glycol, a polypropylene glycol, a polyvinylpyrrolidone (PVP), a polyvinyl alcohol, or any combinations thereof.

10. The composition of claim 9, wherein the alkyl polyethylene oxide comprises at least one selected from the group consisting of a diethylene glycol hexadecyl ether, polyethylene glycol oleyl ether, diethylene glycol octadecyl ether, polyoxyethylene stearyl ether, polyethylene glycol hexadecyl (cetyl) ether, polyethylene glycol dodecyl (lauryl) ether, decaethylene glycol oleyl ether, polyethylene glycol octadecyl ether, and polyethylene glycol octadecyl ether.

11. A method of treating or ameliorating a MUC-1-expressing cancer in a subject in need thereof, comprising administering to the subject a pharmaceutically effective amount of a nanoparticle of claim 1, wherein the composition further comprises at least one chemotherapeutic agent, wherein the chemotherapeutic agent is within the protein nanoparticle, further wherein the composition is administered to the subject by an intrapulmonary, intrabronchial, inhalational, intranasal, intratracheal, intravenous, intramuscular, subcutaneous, topical, transdermal, oral, buccal, rectal, pleural, peritoneal, vaginal, epidural, otic, intraocular, or intrathecal route, and wherein the aptamer binds to MUC-1.

12. The method of claim 11, wherein the MUC-1-expressing cancer is selected from the group consisting of colon cancer, rectum cancer, lung cancer, glioblastoma, renal cell cancer, non-small cell lung cancer, and small cell lung cancer.

13. A kit comprising a composition comprising a nanoparticle of claim 1, the kit further comprising an applicator; and an instructional material for the use of the kit, wherein the instruction material comprises instructions for treating, ameliorating or preventing a disease or disorder in a subject in need thereof.

14. A kit comprising:
a stealth polymer,
at least one protein covalently conjugated to at least one aptamer,
an applicator, and
an instructional material for the use of the kit, wherein the instruction material comprises instructions for preparing a stealth polymer-coated protein nanoparticle,
wherein, in the prepared stealth polymer-coated protein nanoparticle:
the at least one protein covalently conjugated to the at least one aptamer is beneath the stealth polymer layer,
the aptamer spans the stealth polymer layer, and
at least a fraction of the at least one aptamer is displayed on the outer surface of the protein-containing nanoparticle.

* * * * *

UNITED STATES PATENT AND TRADEMARK OFFICE
CERTIFICATE OF CORRECTION

| | | |
|---|---|---|
| PATENT NO. | : 11,484,505 B2 | Page 1 of 1 |
| APPLICATION NO. | : 16/340864 | |
| DATED | : November 1, 2022 | |
| INVENTOR(S) | : Shoyele | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 584 days.

Signed and Sealed this
Fourteenth Day of January, 2025

Derrick Brent
*Acting Director of the United States Patent and Trademark Office*